US007344894B2

(12) United States Patent
Greenstein et al.

(10) Patent No.: US 7,344,894 B2
(45) Date of Patent: Mar. 18, 2008

(54) THERMAL REGULATION OF FLUIDIC SAMPLES WITHIN A DIAGNOSTIC CARTRIDGE

(75) Inventors: Michael Greenstein, Los Altos, CA (US); Frederick Stawitcke, Sunnyvale, CA (US); Vladimir Drbal, Belmont, CA (US); Ganapati R. Mauze, Sunnyvale, CA (US); Rick Pittaro, San Carlos, CA (US); Richard Pering, Mountain View, CA (US); Ed Verdonk, San Jose, CA (US); Don Alden, Sunnyvale, CA (US); Frank Ingle, Palo Alto, CA (US); Klaus Stefan Drese, Mainz (DE); Hans-Joachim Hartmann, Wiesbaden (DE); Olaf Soerensen, Mainz (DE)

(73) Assignee: Agilent Technologies, Inc., Santa Clara, CA (US)

( * ) Notice: Subject to any disclaimer, the term of this patent is extended or adjusted under 35 U.S.C. 154(b) by 229 days.

(21) Appl. No.: 09/981,440

(22) Filed: Oct. 16, 2001

(65) Prior Publication Data

US 2003/0073229 A1 Apr. 17, 2003

(51) Int. Cl.
*G01N 33/543* (2006.01)

(52) U.S. Cl. .................................................... 436/518

(58) Field of Classification Search ................ 436/518, 436/517, 8, 147, 142; 422/50–55, 61, 62, 422/105, 107, 108, 109, 244, 284–290; 435/4, 435/5, 6, 7.1, 287.1, 287.3, 288.4
See application file for complete search history.

(56) References Cited

U.S. PATENT DOCUMENTS

| | | | | |
|---|---|---|---|---|
| 3,358,689 | A | 12/1967 | Higgins | 128/329 |
| 3,494,358 | A | 2/1970 | Grossenbacher | 128/218 |
| 3,626,929 | A | 12/1971 | Sanz | 128/2 R |
| 3,742,954 | A | 7/1973 | Strickland | 128/302 |
| 3,953,172 | A | 4/1976 | Shapiro | 23/230 |
| 4,224,125 | A | 9/1980 | Nakamura | 204/195 B |
| 4,230,118 | A | 10/1980 | Holman et al. | 128/314 |
| 4,338,174 | A | 7/1982 | Tamura | 204/195 |
| 4,340,669 | A | 7/1982 | Bauer | 435/14 |
| 4,353,984 | A | 10/1982 | Yamada | 435/14 |
| 4,360,016 | A | 11/1982 | Sarrine | 128/763 |
| 4,391,905 | A | 7/1983 | Bauer | 435/14 |
| 4,391,906 | A | 7/1983 | Bauer | 435/14 |
| 4,414,975 | A | 11/1983 | Ryder | 128/314 |
| 4,420,564 | A | 12/1983 | Tsuji | 435/288 |
| 4,426,451 | A | 1/1984 | Columbus | 436/518 |
| 4,426,884 | A | 1/1984 | Polchaninoff | 73/172 |
| 4,469,110 | A | 9/1984 | Slama | 128/770 |
| 4,517,978 | A | 5/1985 | Levin | 128/314 |
| 4,539,988 | A | 9/1985 | Shirley | 128/314 |
| 4,545,382 | A | 10/1985 | Higgins | 128/635 |
| 4,553,541 | A | 11/1985 | Burns | 128/314 |
| 4,577,630 | A | 3/1986 | Nitzsche | 128/314 |
| 4,580,564 | A | 4/1986 | Anderson | 502/8 |
| 4,580,565 | A | 4/1986 | Cornell | 128/314 |
| 4,590,411 | A | 5/1986 | Kelly | 318/687 |
| 4,595,479 | A | 6/1986 | Kimura | 204/294 |
| 4,608,997 | A | 9/1986 | Conway | 128/763 |
| 4,615,340 | A | 10/1986 | Cronenberg | 128/635 |
| 4,616,649 | A | 10/1986 | Burns | 128/314 |
| 4,619,754 | A | 10/1986 | Niki | 204/290 |
| 4,622,974 | A | 11/1986 | Coleman | 128/634 |
| 4,624,253 | A | 11/1986 | Burns | 128/314 |
| 4,637,393 | A | 1/1987 | Ray | 128/305 |
| 4,643,189 | A | 2/1987 | Mintz | 128/314 |
| 4,648,408 | A | 3/1987 | Hutcheson | 128/770 |
| 4,653,511 | A | 3/1987 | Goch | 128/763 |
| 4,676,244 | A | 6/1987 | Enstrom | 128/314 |
| 4,677,979 | A | 7/1987 | Burns | 128/314 |
| 4,711,245 | A | 12/1987 | Higgins | 128/635 |
| 4,712,548 | A | 12/1987 | Enstrom | 128/314 |
| 4,715,374 | A | 12/1987 | Maggio | 128/314 |
| 4,735,203 | A | 4/1988 | Ryder | 128/314 |
| 4,758,323 | A | 7/1988 | Davis | 204/403 |
| 4,794,926 | A | 1/1989 | Munsch et al. | 606/183 |
| RE32,922 | E | 3/1989 | Levin | 128/314 |
| 4,814,142 | A | 3/1989 | Gleisner | 422/56 |
| 4,814,661 | A | 3/1989 | Ratzlaff | 310/328 |
| 4,820,010 | A | 4/1989 | Sciefres | 385/43 |
| 4,820,399 | A | 4/1989 | Senda | 204/403 |
| 4,824,639 | A | 4/1989 | Hildenbrand | 422/56 |
| 4,827,763 | A | 5/1989 | Bourland | 73/172 |
| 4,830,959 | A | 5/1989 | McNeil | 435/53 |
| 4,836,904 | A | 6/1989 | Armstron | 204/294 |
| 4,844,095 | A | 7/1989 | Chiodo | 128/314 |
| 4,850,973 | A | 7/1989 | Jordan | 604/157 |
| 4,857,274 | A | 8/1989 | Simon | 422/72 |
| 4,869,249 | A | 9/1989 | Crossman | 128/314 |
| 4,869,265 | A | 9/1989 | McEwen | 128/774 |
| 4,873,993 | A | 10/1989 | Meserol | 128/780 |
| 4,882,013 | A | 11/1989 | Turner | 204/1 |

(Continued)

FOREIGN PATENT DOCUMENTS

| | | |
|---|---|---|
| EP | 0289 269 | 11/1988 |

(Continued)

*Primary Examiner*—Ann Y. Lam

(57) ABSTRACT

A method and miniature analytical device with thermal regulation of reactant using a localized heat source capable of emitting electromagnetic radiation, such as light emitting diodes ("LED"s) and vertical cavity surface emitting lasers ("VCSEL"s), generating internal heat, such as resistive, inductive and Peltier heaters, or external heating. The miniature analytical device comprises of array of temperature-controlled zones to restrict the volume heated and localize the heating by having the localized heat source comprise an array of emitters or heaters.

10 Claims, No Drawings

U.S. PATENT DOCUMENTS

| | | | | |
|---|---|---|---|---|
| 4,883,068 | A | 11/1989 | Dechow | 128/760 |
| 4,886,499 | A | 12/1989 | Cirelli | 604/131 |
| 4,889,529 | A | 12/1989 | Haindl | 604/274 |
| 4,892,097 | A | 1/1990 | Ranalletta | 606/182 |
| 4,895,147 | A | 1/1990 | Bodicky | 606/182 |
| 4,897,173 | A | 1/1990 | Nankai | 204/403 |
| 4,900,424 | A | 2/1990 | Birch | 204/409 |
| 4,911,794 | A | 3/1990 | Parce | 204/1 T |
| 4,920,977 | A | 5/1990 | Haynes | 128/770 |
| 4,945,045 | A | 7/1990 | Forrest | 435/25 |
| 4,948,727 | A | 8/1990 | Cass | 435/18 |
| 4,952,515 | A | 8/1990 | Gleisner | 436/169 |
| 4,953,552 | A | 9/1990 | DeMarzo | 128/635 |
| 4,966,671 | A | 10/1990 | Nylander | 204/153.14 |
| 4,976,724 | A | 12/1990 | Nieto | 606/182 |
| 4,983,178 | A | 1/1991 | Schnell | 606/181 |
| 4,990,154 | A | 2/1991 | Brown | 606/182 |
| 4,999,582 | A | 3/1991 | Parks | 324/438 |
| 5,010,772 | A | 4/1991 | Bourland | 73/862.04 |
| 5,010,774 | A | 4/1991 | Kikuo | 73/862.04 |
| 5,014,718 | A | 5/1991 | Mitchen | 128/771 |
| 5,019,974 | A | 5/1991 | Beckers | 364/413.02 |
| 5,026,388 | A | 6/1991 | Ingalz | 606/182 |
| 5,054,499 | A | 10/1991 | Swierczek | 128/770 |
| 5,059,789 | A | 10/1991 | Salcudean | 435/4 |
| 5,060,174 | A | 10/1991 | Gross | 702/139 |
| 5,070,886 | A | 12/1991 | Mitchen | 128/771 |
| 5,074,872 | A | 12/1991 | Brown | 606/182 |
| 5,089,112 | A | 2/1992 | Skotheim | 204/403 |
| 5,092,842 | A | 3/1992 | Bechtold | 604/135 |
| 5,100,427 | A | 3/1992 | Crossman | 606/182 |
| 5,100,428 | A | 3/1992 | Mumford | 606/182 |
| 5,104,380 | A | 4/1992 | Holman | 604/117 |
| 5,104,619 | A | 4/1992 | Castro | 422/56 |
| 5,108,564 | A | 4/1992 | Szuminsky | 204/153.12 |
| 5,116,759 | A | 5/1992 | Klainer | 435/288 |
| 5,120,420 | A | 6/1992 | Nankai | 204/403 |
| 5,122,244 | A | 6/1992 | Hoenes | 204/153 |
| 5,126,034 | A | 6/1992 | Carter | 204/403 |
| 5,128,015 | A | 7/1992 | Szuminsky | 204/403 |
| 5,128,171 | A | 7/1992 | Gleisner | 427/2 |
| 5,133,730 | A | 7/1992 | Biro | 606/182 |
| 5,139,685 | A | 8/1992 | Castro | 210/767 |
| 5,141,868 | A | 8/1992 | Shanks | 435/288 |
| 5,156,611 | A | 10/1992 | Haynes | 606/181 |
| 5,163,442 | A | 11/1992 | Ono | 128/760 |
| 5,170,364 | A | 12/1992 | Gross | 702/139 |
| D332,490 | S | 1/1993 | Brown | D24/146 |
| 5,178,142 | A | 1/1993 | Harjunmaa | 128/633 |
| 5,181,910 | A | 1/1993 | Scanlon | 604/67 |
| 5,181,914 | A | 1/1993 | Zook | 604/307 |
| 5,183,042 | A | 2/1993 | Harjunmaa | 128/633 |
| 5,185,256 | A | 2/1993 | Nankai | 435/174 |
| 5,187,100 | A | 2/1993 | Matzinger | 436/16 |
| 5,192,415 | A | 3/1993 | Yoshioka | 204/403 |
| 5,196,025 | A | 3/1993 | Ranalletta | 606/182 |
| 5,201,324 | A | 4/1993 | Swierczek | 128/770 |
| 5,205,920 | A | 4/1993 | Oyama | 204/403 |
| 5,212,879 | A | 5/1993 | Biro | 29/437 |
| 5,216,597 | A | 6/1993 | Beckers | 364/413.02 |
| 5,217,480 | A | 6/1993 | Haber | 606/182 |
| 5,228,972 | A | 7/1993 | Osaka | 204/415 |
| 5,229,282 | A | 7/1993 | Yoshioka | 435/177 |
| 5,230,866 | A | 7/1993 | Shartle | 422/103 |
| 5,231,993 | A | 8/1993 | Haber et al. | 128/770 |
| 5,232,667 | A | 8/1993 | Hieb et al. | |
| 5,250,066 | A | 10/1993 | Lambert | 606/181 |
| 5,251,126 | A | 10/1993 | Kahn | 364/413.11 |
| 5,253,656 | A | 10/1993 | Rincoe | 128/782 |
| 5,256,998 | A | 10/1993 | Becker | 335/229 |
| 5,264,103 | A | 11/1993 | Yoshioka | 204/403 |
| 5,264,105 | A | 11/1993 | Gregg | 204/403 |
| 5,264,106 | A | 11/1993 | McAleer | 204/403 |
| 5,266,179 | A | 11/1993 | Nankai | 204/401 |
| D342,673 | S | 12/1993 | Kataoka | D24/147 |
| 5,272,087 | A | 12/1993 | El Murr | 435/291 |
| 5,277,181 | A | 1/1994 | Mendelson | 128/633 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollmann | 435/288 |
| 5,304,192 | A | 4/1994 | Crouse | 606/181 |
| 5,304,193 | A | 4/1994 | Zhadanov | 606/182 |
| 5,312,590 | A | 5/1994 | Gunasingham | 422/56 |
| 5,314,441 | A | 5/1994 | Cusack | 606/182 |
| 5,314,442 | A | 5/1994 | Susumu | 606/182 |
| 5,316,012 | A | 5/1994 | Siegal | 128/744 |
| 5,318,583 | A | 6/1994 | Rabenau | 606/182 |
| 5,320,607 | A | 6/1994 | Ishibashi | 604/115 |
| 5,324,302 | A | 6/1994 | Crouse | 606/181 |
| 5,324,303 | A | 6/1994 | Strong | 606/181 |
| 5,332,479 | A | 7/1994 | Uenoyama | 204/153.12 |
| 5,350,392 | A | 9/1994 | Purcell | 606/182 |
| 5,352,351 | A | 10/1994 | White | 204/406 |
| 5,354,287 | A | 10/1994 | Wacks | 604/232 |
| 5,354,447 | A | 10/1994 | Uenoyama | 204/403 |
| 5,356,420 | A | 10/1994 | Czernecki | 606/182 |
| 5,360,410 | A | 11/1994 | Wacks | 604/232 |
| 5,366,469 | A | 11/1994 | Steg | 606/182 |
| 5,366,470 | A | 11/1994 | Ramel | 606/183 |
| 5,366,609 | A | 11/1994 | White | 204/403 |
| 5,371,687 | A | 12/1994 | Holmes | 364/514 |
| 5,375,397 | A | 12/1994 | Ferrand | 54/66 |
| 5,378,628 | A | 1/1995 | Graetzel | 435/288 |
| 5,382,346 | A | 1/1995 | Uenoyama | 204/403 |
| 5,383,885 | A | 1/1995 | Bland | 606/182 |
| 5,389,534 | A | 2/1995 | Gentezkow | 435/180 |
| 5,393,903 | A | 2/1995 | Graetzel | 556/137 |
| 5,395,387 | A | 3/1995 | Burns | 606/181 |
| 5,397,334 | A | 3/1995 | Schenk | 606/182 |
| 5,401,376 | A | 3/1995 | Foos | 204/415 |
| 5,402,798 | A | 4/1995 | Swierczek | 128/770 |
| 5,405,511 | A | 4/1995 | White | 204/153.1 |
| 5,407,545 | A | 4/1995 | Hirose | 204/153.12 |
| 5,407,554 | A | 4/1995 | Saurer | 204/403 |
| 5,407,818 | A | 4/1995 | Gentzkow | 435/180 |
| 5,409,583 | A | 4/1995 | Yoshioka | 204/153.12 |
| 5,410,059 | A | 4/1995 | Fraser | 546/10 |
| 5,423,847 | A | 6/1995 | Strong et al. | 606/182 |
| 5,436,161 | A | 7/1995 | Bergstrom | 435/291 |
| 5,437,999 | A | 8/1995 | Diebold | 435/288 |
| 5,438,271 | A | 8/1995 | White | 324/444 |
| 5,443,701 | A | 8/1995 | Willner | 204/153 |
| 5,445,920 | A | 8/1995 | Saito | 430/311 |
| D362,719 | S | 9/1995 | Kaplan | D24/147 |
| 5,454,828 | A | 10/1995 | Schraga | 606/181 |
| 5,456,875 | A | 10/1995 | Lambert | 264/328.1 |
| 5,464,418 | A | 11/1995 | Schraga | 606/182 |
| 5,471,102 | A | 11/1995 | Becker | 310/50 |
| 5,476,474 | A | 12/1995 | Davis | 606/182 |
| 5,480,387 | A | 1/1996 | Gabriel | 604/134 |
| 5,487,748 | A | 1/1996 | Marshall | 606/182 |
| 5,496,453 | A | 3/1996 | Uenoyama | 205/777.5 |
| 5,498,542 | A | 3/1996 | Corey | 435/283.1 |
| 5,507,288 | A | 4/1996 | Bocker | 128/633 |
| 5,508,171 | A | 4/1996 | Walling | 205/777.5 |
| 5,509,410 | A | 4/1996 | Hill | 128/637 |
| 5,510,266 | A | 4/1996 | Bonner et al. | 436/43 |
| 5,512,159 | A | 4/1996 | Yoshioka | 204/403 |
| 5,518,006 | A | 5/1996 | Mawhirt | 128/770 |
| 5,524,636 | A | 6/1996 | Sarvazyan | 128/774 |
| 5,525,511 | A | 6/1996 | D'Costa | 435/287.9 |
| 5,527,333 | A | 6/1996 | Nikkels | 606/182 |
| 5,527,334 | A | 6/1996 | Kanner | 606/182 |

| | | | | |
|---|---|---|---|---|
| 5,540,709 | A | 7/1996 | Ramel | 606/183 |
| 5,543,326 | A | 8/1996 | Heller | 435/287.9 |
| 5,545,174 | A | 8/1996 | Schenk | 606/182 |
| 5,547,702 | A | 8/1996 | Gleisner | 427/2.13 |
| 5,554,166 | A | 9/1996 | Lange | 606/182 |
| 5,558,834 | A | 9/1996 | Chu | 422/55 |
| 5,569,286 | A | 10/1996 | Peckham | 606/181 |
| 5,569,287 | A | 10/1996 | Tezuka | 606/182 |
| 5,571,132 | A | 11/1996 | Mawhirt | 606/182 |
| 5,575,895 | A | 11/1996 | Ikeda | 204/403 |
| 5,582,697 | A | 12/1996 | Ikeda | 204/403 |
| 5,584,846 | A | 12/1996 | Mawhirt | 606/181 |
| 5,593,852 | A | 1/1997 | Heller | 435/14 |
| 5,594,751 | A * | 1/1997 | Scott | 372/46.013 |
| 5,599,502 | A * | 2/1997 | Miyazaki et al. | 422/82.01 |
| 5,609,749 | A | 3/1997 | Yamauchi | 205/777.5 |
| 5,613,978 | A | 3/1997 | Harding | 606/181 |
| 5,620,579 | A | 4/1997 | Genshaw | 204/402 |
| 5,624,537 | A | 4/1997 | Turner | 204/403 |
| D379,516 | S | 5/1997 | Rutter | D24/146 |
| 5,628,764 | A | 5/1997 | Schraga | 606/182 |
| 5,628,765 | A | 5/1997 | Susumu | 606/182 |
| 5,628,890 | A | 5/1997 | Carter | 204/403 |
| 5,640,954 | A | 6/1997 | Pfeiffer | 128/635 |
| 5,643,306 | A | 7/1997 | Schraga | 606/182 |
| 5,645,555 | A | 7/1997 | Davis | 606/182 |
| 5,650,062 | A | 7/1997 | Ikeda | 205/778 |
| 5,653,863 | A | 8/1997 | Genshaw | 205/777.5 |
| 5,657,760 | A | 8/1997 | Ying et al. | 128/660.03 |
| 5,658,444 | A | 8/1997 | Black | 204/415 |
| 5,662,127 | A | 9/1997 | De Vaughn | 128/765 |
| 5,662,672 | A | 9/1997 | Pambianchi | 606/181 |
| 5,676,143 | A | 10/1997 | Simonsen | 128/633 |
| 5,680,858 | A | 10/1997 | Henrik-Egesborg | 128/635 |
| 5,680,872 | A | 10/1997 | Sesekura | 128/760 |
| 5,682,884 | A | 11/1997 | Hill | 128/637 |
| 5,683,562 | A | 11/1997 | Schaffar | 204/403 |
| 5,695,947 | A | 12/1997 | Guo | 435/11 |
| 5,700,695 | A | 12/1997 | Yassinzadeh | 436/180 |
| 5,705,045 | A | 1/1998 | Park | 204/403 |
| 5,707,139 | A | 1/1998 | Haitz | |
| 5,708,247 | A | 1/1998 | McAleer | 204/403 |
| 5,709,668 | A | 1/1998 | Wacks | 604/232 |
| 5,709,699 | A | 1/1998 | Warner | 606/181 |
| 5,710,011 | A | 1/1998 | Forrow | 435/25 |
| 5,720,862 | A | 2/1998 | Hamamoto | 204/403 |
| 5,720,924 | A | 2/1998 | Eikmeier | 422/102 |
| D392,391 | S | 3/1998 | Douglas | D24/225 |
| 5,723,284 | A | 3/1998 | Ye | 435/4 |
| 5,727,548 | A | 3/1998 | Hill | 128/637 |
| 5,730,753 | A | 3/1998 | Susumu | 606/181 |
| 5,733,300 | A | 3/1998 | Pambianchi | 606/181 |
| D393,716 | S | 4/1998 | Brenneman | D24/147 |
| D393,717 | S | 4/1998 | Brenneman | D24/147 |
| 5,741,228 | A | 4/1998 | Lambrecht | 604/93 |
| 5,741,634 | A | 4/1998 | Nozoe | 435/4 |
| RE35,803 | E | 5/1998 | Lange | 606/182 |
| 5,746,217 | A | 5/1998 | Erickson | 128/760 |
| 5,746,898 | A | 5/1998 | Preidel | 204/403 |
| 5,755,733 | A | 5/1998 | Susumu | 606/182 |
| 5,759,364 | A | 6/1998 | Charlton | 204/403 |
| 5,762,770 | A | 6/1998 | Pritchard | 204/403 |
| 5,770,369 | A | 6/1998 | Meade | 435/6 |
| 5,772,586 | A | 6/1998 | Heinonen | 600/300 |
| 5,772,677 | A | 6/1998 | Mawhirt | 606/181 |
| 5,773,270 | A | 6/1998 | D'Orazio | 435/177 |
| 5,776,719 | A | 7/1998 | Douglas | 435/28 |
| 5,782,770 | A | 7/1998 | Mooradian | 600/476 |
| 5,782,852 | A | 7/1998 | Foggia | 606/182 |
| 5,788,652 | A | 8/1998 | Rahn | 600/577 |
| 5,794,219 | A | 8/1998 | Brown | 705/37 |
| 5,795,725 | A | 8/1998 | Buechler | 435/7.1 |
| 5,795,774 | A | 8/1998 | Matsumoto | 435/287.9 |
| 5,797,940 | A | 8/1998 | Mawhirt | 606/167 |
| 5,797,942 | A | 8/1998 | Schraga | 606/182 |
| 5,798,030 | A | 8/1998 | Raguse | 204/403 |
| 5,798,031 | A | 8/1998 | Charlton | 204/403 |
| 5,800,781 | A | 9/1998 | Gavin et al. | 422/73 |
| 5,801,057 | A | 9/1998 | Smart | 436/68 |
| 5,807,375 | A | 9/1998 | Gross | 604/890.1 |
| 5,820,551 | A | 10/1998 | Hill | 600/347 |
| 5,822,715 | A | 10/1998 | Worthington | 702/19 |
| 5,824,491 | A | 10/1998 | Priest | 435/28 |
| 5,828,943 | A | 10/1998 | Brown | 434/258 |
| 5,832,448 | A | 11/1998 | Brown | 705/2 |
| 5,840,020 | A | 11/1998 | Heinonen | 600/309 |
| 5,840,171 | A | 11/1998 | Birch | 205/335 |
| 5,849,174 | A | 12/1998 | Sanghera | 205/775 |
| 5,853,373 | A | 12/1998 | Griffith | 600/554 |
| D403,975 | S | 1/1999 | Douglas | D10/81 |
| 5,857,983 | A | 1/1999 | Douglas | 600/538 |
| 5,860,922 | A | 1/1999 | Gordon et al. | 600/431 |
| 5,866,353 | A | 2/1999 | Berneth | 435/26 |
| 5,868,135 | A | 2/1999 | Kaufman | 128/630 |
| 5,868,772 | A | 2/1999 | LeVaughn | 606/181 |
| 5,869,972 | A | 2/1999 | Birch | 324/439 |
| 5,872,713 | A | 2/1999 | Douglas | 702/85 |
| 5,873,887 | A | 2/1999 | King | 606/182 |
| 5,876,957 | A | 3/1999 | Douglas | 435/28 |
| 5,879,163 | A | 3/1999 | Brown | 434/236 |
| 5,879,310 | A | 3/1999 | Sopp | 600/578 |
| 5,879,373 | A | 3/1999 | Roper | 606/344 |
| 5,882,494 | A | 3/1999 | van Antwerp | 204/403 |
| 5,885,211 | A | 3/1999 | Eppstein | 600/309 |
| 5,887,133 | A | 3/1999 | Brown | 395/200.3 |
| RE36,191 | E | 4/1999 | Solomon | 395/308 |
| 5,893,870 | A | 4/1999 | Talen | 606/201 |
| 5,897,493 | A | 4/1999 | Brown | 600/300 |
| 5,899,855 | A | 5/1999 | Brown | 600/301 |
| 5,900,130 | A | 5/1999 | Benvegnu | 204/453 |
| 5,906,921 | A | 5/1999 | Ikeda | 435/25 |
| D411,619 | S | 6/1999 | Duchon | D24/146 |
| 5,913,310 | A | 6/1999 | Brown | 128/897 |
| 5,916,156 | A | 6/1999 | Hildenbrand | 600/347 |
| 5,916,229 | A | 6/1999 | Evans | 606/171 |
| 5,916,230 | A | 6/1999 | Brenneman | 606/172 |
| 5,918,603 | A | 7/1999 | Brown | 128/897 |
| 5,921,963 | A | 7/1999 | Erez | 604/192 |
| 5,922,188 | A | 7/1999 | Ikeda | 204/777.5 |
| RE36,268 | E | 8/1999 | Szuminsky | 205/777.5 |
| 5,933,136 | A | 8/1999 | Brown | 345/327 |
| 5,935,075 | A | 8/1999 | Casscells et al. | 600/474 |
| 5,942,102 | A | 8/1999 | Hodges | 205/775 |
| 5,951,300 | A | 9/1999 | Brown | 434/236 |
| 5,951,492 | A | 9/1999 | Douglas | 600/583 |
| 5,951,836 | A | 9/1999 | McAleer | 204/403 |
| 5,954,738 | A | 9/1999 | LeVaughn | 606/181 |
| 5,956,501 | A | 9/1999 | Brown | 395/500.32 |
| 5,958,199 | A | 9/1999 | Miyamoto | 204/403 |
| 5,960,403 | A | 9/1999 | Brown | 705/2 |
| 5,964,718 | A | 10/1999 | Duchon | 600/583 |
| 5,965,380 | A | 10/1999 | Heller | 435/14 |
| 5,965,410 | A | 10/1999 | Chow et al. | |
| 5,972,199 | A | 10/1999 | Heller | 205/777.5 |
| 5,972,715 | A | 10/1999 | Celentano | 436/164 |
| 5,974,124 | A | 10/1999 | Schlueter | 379/106.02 |
| 5,983,193 | A | 11/1999 | Heinonen | 705/2 |
| 5,985,116 | A | 11/1999 | Ikeda | 204/403 |
| 5,985,559 | A | 11/1999 | Brown | 435/6 |
| 5,993,400 | A | 11/1999 | Rincoe | 600/595 |
| 5,997,476 | A | 12/1999 | Brown | 600/300 |
| 5,997,561 | A | 12/1999 | Boecker | 606/182 |
| 5,997,817 | A | 12/1999 | Crismore | 422/58 |
| 5,997,818 | A | 12/1999 | Hacker | 422/681 |
| 6,001,067 | A | 12/1999 | Shults | 600/584 |
| 6,015,392 | A | 1/2000 | Douglas | 600/583 |

| | | | | |
|---|---|---|---|---|
| 6,020,110 | A | 2/2000 | Williams | 430/315 |
| 6,022,324 | A | 2/2000 | Skinner | 600/566 |
| 6,022,366 | A | 2/2000 | Schraga | 606/181 |
| 6,023,686 | A | 2/2000 | Brown | 705/37 |
| 6,030,399 | A | 2/2000 | Ignotz | 606/167 |
| 6,030,827 | A | 2/2000 | Davis | 435/287 |
| 6,032,119 | A | 2/2000 | Brown | 705/2 |
| 6,033,421 | A | 3/2000 | Theiss | 606/186 |
| 6,033,866 | A | 3/2000 | Guo | 435/14 |
| 6,041,253 | A | 3/2000 | Kost | 604/20 |
| 6,048,352 | A | 4/2000 | Douglas | 606/181 |
| D424,696 | S | 5/2000 | Ray | D24/169 |
| 6,056,701 | A | 5/2000 | Duchon | 600/583 |
| 6,060,327 | A | 5/2000 | Keen | 436/518 |
| 6,061,128 | A | 5/2000 | Zweig | 356/243.4 |
| 6,063,039 | A | 5/2000 | Cunningham | 600/573 |
| 6,066,103 | A | 5/2000 | Duchon | 600/583 |
| 6,066,243 | A | 5/2000 | Anderson et al. | |
| 6,066,296 | A | 5/2000 | Brady | 422/63 |
| 6,067,463 | A | 5/2000 | Jeng | 600/336 |
| 6,068,615 | A | 5/2000 | Brown | 604/207 |
| D426,638 | S | 6/2000 | Ray | D24/169 |
| 6,071,249 | A | 6/2000 | Cunningham | 600/578 |
| 6,071,250 | A | 6/2000 | Douglas | 600/583 |
| 6,071,251 | A | 6/2000 | Cunningham | 600/584 |
| 6,074,360 | A | 6/2000 | Haar et al. | 604/57 |
| 6,077,408 | A | 6/2000 | Miyamoto | 204/403 |
| 6,080,172 | A | 6/2000 | Fujiwara | 606/166 |
| 6,083,710 | A | 7/2000 | Heller | 435/14 |
| 6,085,576 | A | 7/2000 | Sunshine et al. | |
| 6,086,545 | A | 7/2000 | Roe | 600/570 |
| 6,086,562 | A | 7/2000 | Jacobsen | 604/156 |
| 6,090,078 | A | 7/2000 | Erskine | 604/198 |
| 6,093,146 | A | 7/2000 | Filangeri | 600/300 |
| 6,101,478 | A | 8/2000 | Brown | 705/2 |
| 6,103,033 | A | 8/2000 | Say | 156/73.1 |
| 6,107,083 | A | 8/2000 | Collins | 435/288 |
| 6,113,578 | A | 9/2000 | Brown | 604/207 |
| 6,120,676 | A | 9/2000 | Heller | 205/777.5 |
| 6,121,009 | A | 9/2000 | Heller | 435/14 |
| 6,122,536 | A | 9/2000 | Sun | 600/341 |
| 6,129,823 | A | 10/2000 | Hughes | 204/403.01 |
| 6,132,580 | A | 10/2000 | Mathies et al. | |
| 6,133,837 | A | 10/2000 | Riley | 340/573.1 |
| 6,134,461 | A | 10/2000 | Say | 600/345 |
| 6,144,837 | A | 11/2000 | Quy | 434/307 R |
| 6,151,586 | A | 11/2000 | Brown | 705/14 |
| 6,153,069 | A | 11/2000 | Pottgen | 204/403 |
| RE36,991 | E | 12/2000 | Yamamoto et al. | 204/403 |
| 6,155,267 | A | 12/2000 | Nelson | 128/899 |
| 6,155,992 | A | 12/2000 | Henning et al. | 600/583 |
| 6,157,442 | A | 12/2000 | Raskas | 356/39 |
| 6,161,095 | A | 12/2000 | Brown | 705/2 |
| 6,162,611 | A | 12/2000 | Heller | 435/14 |
| 6,167,362 | A | 12/2000 | Brown | 703/11 |
| 6,167,386 | A | 12/2000 | Brown | 705/37 |
| 6,168,563 | B1 | 1/2001 | Brown | 600/301 |
| 6,175,752 | B1 | 1/2001 | Say | 600/345 |
| 6,177,000 | B1 | 1/2001 | Peterson | 205/777.5 |
| 6,186,145 | B1 | 2/2001 | Brown | 128/897 |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,194,900 | B1 | 2/2001 | Freeman | 324/321 |
| 6,197,257 | B1 | 3/2001 | Raskas | 422/82.05 |
| 6,203,683 | B1 * | 3/2001 | Austin et al. | 204/547 |
| 6,206,841 | B1 | 3/2001 | Cunningham et al. | 600/584 |
| 6,210,272 | B1 | 4/2001 | Brown | 463/1 |
| 6,210,882 | B1 | 4/2001 | Landers et al. | |
| 6,212,417 | B1 | 4/2001 | Ikeda | 204/403.14 |
| 6,214,804 | B1 | 4/2001 | Felgner | 514/44 |
| 6,221,238 | B1 | 4/2001 | Grundig | 205/777.5 |
| 6,225,078 | B1 | 5/2001 | Ikeda | 435/25 |
| 6,230,501 | B1 | 5/2001 | Bailey | 62/51.1 |
| 6,233,471 | B1 | 5/2001 | Berner | 600/345 |
| 6,233,539 | B1 | 5/2001 | Brown | 703/11 |
| 6,240,393 | B1 | 5/2001 | Brown | 705/1 |
| 6,241,862 | B1 | 6/2001 | McAleer | 204/403 |
| 6,245,060 | B1 | 6/2001 | Loomis | 606/9 |
| 6,246,992 | B1 | 6/2001 | Brown | 705/2 |
| 6,248,065 | B1 | 6/2001 | Brown | 600/300 |
| 6,251,260 | B1 | 6/2001 | Heller | 205/777.5 |
| 6,254,831 | B1 | 7/2001 | Barnard | 422/82.08 |
| 6,256,533 | B1 | 7/2001 | Vuzhakov | 604/21 |
| 6,258,229 | B1 | 7/2001 | Winarta | 204/403 |
| 6,258,254 | B1 | 7/2001 | Miyamoto | 205/777.5 |
| 6,268,161 | B1 | 7/2001 | Han | 435/14 |
| 6,270,455 | B1 | 8/2001 | Brown | 600/300 |
| 6,270,637 | B1 | 8/2001 | Crismore | 204/403 |
| 6,272,359 | B1 | 8/2001 | Kivela | 455/567 |
| 6,281,006 | B1 | 8/2001 | Heller | 435/287.9 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |
| 6,290,683 | B1 | 9/2001 | Erez | 604/723 |
| 6,294,897 | B1 | 9/2001 | Champlin | 320/153 |
| 6,295,506 | B1 | 9/2001 | Heinonen | 702/104 |
| 6,299,757 | B1 | 10/2001 | Feldman | 205/775 |
| 6,302,844 | B1 | 10/2001 | Walker | 600/300 |
| 6,302,855 | B1 | 10/2001 | Lav | 600/584 |
| 6,305,804 | B1 | 10/2001 | Rice | 351/221 |
| 6,306,347 | B1 | 10/2001 | Mason | 422/58 |
| 6,309,535 | B1 | 10/2001 | Williams | 205/777.5 |
| 6,312,612 | B1 | 11/2001 | Sherman | 216/2 |
| 6,322,574 | B1 | 11/2001 | Lloyd | 606/181 |
| 6,329,161 | B1 | 12/2001 | Heller | 435/14 |
| 6,330,426 | B2 | 12/2001 | Brown | 434/307 R |
| 6,331,163 | B1 | 12/2001 | Kaplan | 600/486 |
| 6,334,363 | B1 | 1/2002 | Testud | 73/862 |
| 6,334,778 | B1 | 1/2002 | Brown | 434/258 |
| 6,334,856 | B1 | 1/2002 | Allen | 604/191 |
| 6,338,790 | B1 | 1/2002 | Feldman | 205/777.5 |
| 6,349,229 | B1 | 2/2002 | Watanabe | 600/345 |
| 6,350,273 | B1 | 2/2002 | Minagawa | 606/186 |
| 6,350,451 | B1 | 2/2002 | Horn | 424/184.1 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri et al. | 606/181 |
| 6,368,273 | B1 | 4/2002 | Brown | 600/300 |
| 6,375,469 | B1 | 4/2002 | Brown | 434/236 |
| 6,379,301 | B1 | 4/2002 | Worthington | 600/309 |
| 6,379,324 | B1 | 4/2002 | Gartstein | 604/22 |
| 6,379,929 | B1 * | 4/2002 | Burns et al. | 435/91.2 |
| 6,381,577 | B1 | 4/2002 | Brown | 705/2 |
| 6,387,709 | B1 | 5/2002 | Mason | 436/164 |
| 6,399,394 | B1 | 6/2002 | Dahm | 436/180 |
| 6,413,410 | B1 | 7/2002 | Hodges | 205/775 |
| 6,413,411 | B1 | 7/2002 | Pottgen | 205/777.5 |
| 6,421,633 | B1 | 7/2002 | Heinonen | 703/11 |
| 6,428,664 | B1 | 8/2002 | Bhullar | 204/403.03 |
| 6,436,256 | B1 | 8/2002 | Williams | 204/403.06 |
| 6,436,721 | B1 | 8/2002 | Kuo | 436/514 |
| 6,440,645 | B1 | 8/2002 | Yon-Hin | 430/322 |
| 6,440,725 | B1 * | 8/2002 | Pourahmadi et al. | 435/288 |
| 6,451,040 | B1 | 9/2002 | Purcell | 606/181 |
| 6,458,258 | B2 | 10/2002 | Taniike | 204/403 |
| 6,462,162 | B2 | 10/2002 | van Antwerp | 528/77 |
| 6,464,649 | B1 | 10/2002 | Duchon | 600/583 |
| 6,471,903 | B2 | 10/2002 | Sherman | 264/328.1 |
| 6,475,436 | B1 | 11/2002 | Schabbach | 422/64 |
| 6,477,394 | B2 | 11/2002 | Rice | 600/318 |
| 6,477,424 | B1 | 11/2002 | Thompson | 607/60 |
| 6,484,046 | B1 | 11/2002 | Say | 600/345 |
| 6,745,750 | B2 | 11/2002 | Han | 435/14 |
| 6,489,052 | B1 | 12/2002 | Acker | 600/584 |
| 6,494,830 | B1 | 12/2002 | Wessel | 600/300 |

| | | | | |
|---|---|---|---|---|
| 6,501,404 | B2 | 12/2002 | Walker | 341/143 |
| 6,503,231 | B1 | 1/2003 | Praunsnitz | 604/272 |
| 6,503,381 | B1 | 1/2003 | Gotoh | 204/403.14 |
| 6,506,168 | B1 | 1/2003 | Fathallah | 600/578 |
| 6,508,795 | B1 | 1/2003 | Samuelsson | 604/113 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor | 206/305 |
| 6,527,778 | B2 | 3/2003 | Athanasiou | 606/80 |
| 6,530,892 | B1 | 3/2003 | Kelly | 600/583 |
| 6,530,937 | B1 | 3/2003 | Schraga | 606/182 |
| 6,533,949 | B1 | 3/2003 | Yeshurun | 216/11 |
| 6,537,207 | B1 | 3/2003 | Rice | 600/121 |
| 6,537,242 | B1 | 3/2003 | Palmer | 604/22 |
| 6,537,292 | B1 | 3/2003 | Lee | 606/182 |
| 6,540,672 | B1 | 4/2003 | Simonsen | 600/300 |
| 6,540,675 | B2 | 4/2003 | Aceti | 600/309 |
| 6,540,762 | B1 | 4/2003 | Bertling | 606/182 |
| 6,540,891 | B1 | 4/2003 | Stewart | 204/403.14 |
| 6,541,266 | B2 | 4/2003 | Modzelewski | 436/95 |
| 6,547,954 | B2 | 4/2003 | Ikeda | 205/777.5 |
| 6,549,690 | B2 * | 4/2003 | Schulte et al. | 385/17 |
| 6,549,796 | B2 | 4/2003 | Sohrab | 600/345 |
| 6,551,494 | B1 | 4/2003 | Heller | 205/777.5 |
| 6,553,244 | B2 | 4/2003 | Lesho | 600/347 |
| 6,554,381 | B2 | 4/2003 | Locher | 347/7 |
| 6,555,061 | B1 | 4/2003 | Leong | 422/58 |
| 6,558,320 | B1 | 5/2003 | Causey | 600/300 |
| 6,558,361 | B1 | 5/2003 | Yeshurun | 604/272 |
| 6,558,402 | B1 | 5/2003 | Chelak | 606/182 |
| 6,558,528 | B1 | 5/2003 | Matzinger | 205/777.5 |
| 6,560,471 | B1 | 5/2003 | Heller | 600/347 |
| 6,561,978 | B1 | 5/2003 | Conn | 600/309 |
| 6,561,989 | B2 | 5/2003 | Whitson | 600/573 |
| 6,562,210 | B1 | 5/2003 | Bhullar | 204/403.3 |
| 6,565,509 | B1 | 5/2003 | Say | 600/365 |
| 6,565,808 | B2 | 5/2003 | Hudak | 422/58 |
| 6,569,157 | B1 | 5/2003 | Shain | 606/12 |
| 6,571,651 | B1 | 6/2003 | Hodges | 73/864.72 |
| 6,572,566 | B2 | 6/2003 | Effenhauser | 600/584 |
| 6,574,490 | B2 | 6/2003 | Abbink | 600/316 |
| 6,575,905 | B2 | 6/2003 | Knobbe | 600/365 |
| 6,576,101 | B1 | 6/2003 | Heller | 204/403.14 |
| 6,576,117 | B1 | 6/2003 | Kazuo | 205/777.5 |
| 6,576,416 | B2 | 6/2003 | Haviland | 435/4 |
| 6,582,573 | B2 | 6/2003 | Douglas | 204/403.1 |
| 6,587,705 | B1 | 7/2003 | Kim | 600/347 |
| 6,589,260 | B1 | 7/2003 | Schmelzeisen-R | 606/181 |
| 6,589,261 | B1 | 7/2003 | Abulhaj | 606/181 |
| 6,591,125 | B1 | 7/2003 | Buse | 600/347 |
| 6,592,745 | B1 | 7/2003 | Feldman | 205/777.5 |
| 6,595,919 | B2 | 7/2003 | Berner | 600/365 |
| 6,599,407 | B2 | 7/2003 | Taniike | 204/403.1 |
| 6,599,693 | B1 | 7/2003 | Webb | 435/4 |
| 6,602,205 | B1 | 8/2003 | Erickson | 600/573 |
| 6,602,268 | B2 | 8/2003 | Kuhr | 606/181 |
| 6,602,678 | B2 | 8/2003 | Kwon | 435/14 |
| 6,604,050 | B2 | 8/2003 | Trippel | 702/19 |
| 6,607,494 | B1 | 8/2003 | Fowler | 600/570 |
| 6,607,658 | B1 | 8/2003 | Heller | 205/777.5 |
| 6,616,616 | B2 | 9/2003 | Fritz | 600/583 |
| 6,616,819 | B1 | 9/2003 | Liamos | 204/403.02 |
| 6,618,934 | B1 | 9/2003 | Feldman | 29/830 |
| 6,620,112 | B2 | 9/2003 | Klitmose | 600/583 |
| 6,623,501 | B2 | 9/2003 | Heller | 606/181 |
| 6,626,851 | B2 | 9/2003 | Hirao | 600/576 |
| 6,635,222 | B2 | 10/2003 | Kent | 422/22 |
| 6,638,772 | B1 | 10/2003 | Douglas | 436/518 |
| 6,641,533 | B2 | 11/2003 | Causey | 600/300 |
| 6,645,142 | B2 | 11/2003 | Braig | 600/300 |
| 6,645,219 | B2 | 11/2003 | Roe | 606/182 |
| 6,645,368 | B1 | 11/2003 | Beatty | 205/792 |
| 6,650,915 | B2 | 11/2003 | Routt | 600/319 |
| 6,652,720 | B1 | 11/2003 | Mansouri | 204/403.11 |
| 6,656,702 | B1 | 12/2003 | Yugawa | 435/26 |
| 6,659,966 | B2 | 12/2003 | Essenpreis | 600/583 |
| 6,660,018 | B2 | 12/2003 | Lum | 606/181 |
| 6,671,527 | B2 | 12/2003 | Petersson | 600/316 |
| 6,679,841 | B2 | 1/2004 | Bojan | 600/309 |
| 6,679,852 | B1 | 1/2004 | Schmelzeisen-R | 600/583 |
| 6,706,000 | B2 | 3/2004 | Perez | 600/583 |
| 6,706,049 | B2 | 3/2004 | Moerman | 606/181 |
| 6,706,159 | B2 | 3/2004 | Moerman | 204/403.03 |
| 6,706,232 | B2 | 3/2004 | Hasegawa | 264/403.09 |
| 6,713,660 | B1 | 3/2004 | Roe | 604/361 |
| 6,719,449 | B1 * | 4/2004 | Laugharn et al. | 366/127 |
| 6,719,887 | B2 | 4/2004 | Hasegawa | 204/403.09 |
| 6,719,921 | B2 | 4/2004 | Stiene | 252/511 |
| 6,721,586 | B2 | 4/2004 | Kiser | 600/345 |
| 6,723,046 | B2 | 4/2004 | Lichtenstein | 600/300 |
| 6,723,111 | B2 | 4/2004 | Abulhaj | 606/181 |
| 6,723,371 | B2 | 4/2004 | Chih-hui | 472/2.13 |
| 6,723,500 | B2 | 4/2004 | Yu | 435/4 |
| 6,726,818 | B2 | 4/2004 | Cui et al. | 204/403.01 |
| 6,733,493 | B2 | 5/2004 | Gruzdev | 606/9 |
| 6,736,777 | B2 | 5/2004 | Kim | 600/365 |
| 6,740,215 | B1 | 5/2004 | Yamamoto | 204/403.14 |
| 6,743,211 | B1 | 6/2004 | Prausnitz | 604/239 |
| 6,743,635 | B2 | 6/2004 | Neel | 436/95 |
| 6,749,618 | B2 | 6/2004 | Levaughn | 606/182 |
| 6,749,792 | B2 | 6/2004 | Olsen | 264/328.1 |
| 6,751,491 | B2 | 6/2004 | Lew | 600/345 |
| 6,752,817 | B2 | 6/2004 | Flora | 606/181 |
| 6,759,190 | B2 | 7/2004 | Lin | 435/4 |
| 6,762,049 | B2 * | 7/2004 | Zou et al. | 435/287.2 |
| 6,764,496 | B2 | 7/2004 | Schraga | 606/182 |
| 6,764,581 | B1 | 7/2004 | Forrow | 204/403 |
| 6,767,441 | B1 | 7/2004 | Cai | 204/403.03 |
| 6,773,671 | B1 | 8/2004 | Lewis | 422/58 |
| 6,776,888 | B2 | 8/2004 | Yamamoto | 204/403.06 |
| 6,780,645 | B2 | 8/2004 | Hayter | 436/8 |
| 6,780,647 | B2 | 8/2004 | Fujiwara | 436/169 |
| 6,783,502 | B2 | 8/2004 | Orloff | 600/583 |
| 6,783,537 | B1 | 8/2004 | Kuhr | 606/182 |
| 6,784,274 | B2 | 8/2004 | van Antwerp | 528/77 |
| 6,786,874 | B2 | 9/2004 | Grace | 600/573 |
| 6,787,013 | B2 | 9/2004 | Chang | 204/412 |
| 6,787,109 | B2 | 9/2004 | Haar | 422/82.05 |
| 6,790,327 | B2 | 9/2004 | Ikeda | 204/403.1 |
| 6,790,599 | B1 | 9/2004 | Madou | 430/320 |
| 6,792,791 | B2 | 9/2004 | Sato | 73/1.02 |
| 6,793,632 | B2 | 9/2004 | Sohrab | 600/573 |
| 6,793,633 | B2 | 9/2004 | Douglas | 600/583 |
| 6,793,802 | B2 | 9/2004 | Lee | 205/777.5 |
| 6,797,150 | B2 | 9/2004 | Kermani | 205/777.5 |
| 6,800,488 | B2 | 10/2004 | Khan | 436/166 |
| 6,801,041 | B2 | 10/2004 | Karinka | 324/444 |
| 6,801,804 | B2 | 10/2004 | Miller | 604/20 |
| 6,802,199 | B2 | 10/2004 | Hilgers | 72/370.1 |
| 6,802,811 | B1 | 10/2004 | Slepian | 600/309 |
| 6,802,957 | B2 | 10/2004 | Jung | 205/777.5 |
| 6,805,780 | B1 | 10/2004 | Ryu | 204/403.01 |
| 6,808,499 | B1 | 10/2004 | Churchill | 600/587 |
| 6,808,908 | B2 | 10/2004 | Yao | 435/181 |
| 6,808,937 | B2 | 10/2004 | Ligler | 436/518 |
| 6,809,807 | B1 | 10/2004 | Erickson | 356/213 |
| 6,811,557 | B2 | 11/2004 | Schraga | 606/182 |
| 6,811,659 | B2 | 11/2004 | Vachon | 204/224 |
| 6,811,753 | B2 | 11/2004 | Hirao | 422/101 |
| 6,811,792 | B2 | 11/2004 | Roser | 424/423 |
| 6,812,031 | B1 | 11/2004 | Carlsson | 436/52 |
| 6,814,843 | B1 | 11/2004 | Bhullar | 204/403.01 |
| 6,814,844 | B2 | 11/2004 | Bhullar | 204/403.1 |
| 6,814,845 | B2 | 11/2004 | Wilson | 204/486 |
| 6,815,186 | B2 | 11/2004 | Clark | 435/183 |

6,816,742 B2 11/2004 Kim ........................... 600/345
6,818,180 B2 11/2004 Douglas ...................... 422/58
6,821,483 B2 11/2004 Phillips ...................... 422/58
6,823,750 B2 11/2004 Hodges ................... 73/864.72
6,825,047 B1 11/2004 Woudenberg ............... 436/518
6,827,250 B2 12/2004 Uhland .................... 228/110.1
6,827,829 B2 12/2004 Kawanaka ............. 204/403.02
6,830,551 B1 12/2004 Uchigaki ................... 600/584
6,830,668 B2 12/2004 Musho ....................... 204/400
6,830,669 B2 12/2004 Miyazaki .................... 204/409
6,833,540 B2 12/2004 MacKenzie ................. 250/214
6,835,184 B1 12/2004 Sage .......................... 604/46
6,835,553 B2 12/2004 Han ........................... 435/14
6,837,858 B2 1/2005 Cunningham ............... 600/573
6,837,976 B2 1/2005 Cai ....................... 204/403.14
6,837,988 B2 1/2005 Leong ........................ 205/792
6,840,912 B2 1/2005 Kloepfer ..................... 600/583
6,841,052 B2 1/2005 Musho ....................... 204/401
6,843,254 B2 1/2005 Tapper ....................... 128/898
6,847,451 B2 1/2005 Pugh .......................... 356/436
6,849,168 B2 2/2005 Crumly ...................... 204/416
6,849,216 B2 2/2005 Rappin ....................... 264/134
6,850,790 B2 2/2005 Berner ....................... 600/347
6,869,418 B2 3/2005 Marano-Ford .............. 604/192
6,872,200 B2 3/2005 Mann ...................... 604/890.1
6,875,208 B2 4/2005 Santini .................... 604/890.1
6,875,223 B2 4/2005 Argauer ...................... 606/181
6,875,613 B2 4/2005 Shartle ........................ 436/63
6,878,120 B2 4/2005 Roe ........................... 600/583
6,878,251 B2 4/2005 Hodges ................. 204/403.14
6,878,255 B1 4/2005 Wang ......................... 204/452
6,878,262 B2 4/2005 Taniike .................... 205/777.5
6,880,968 B1 4/2005 Haar .......................... 374/131
6,881,203 B2 4/2005 Delmore ..................... 604/272
6,881,322 B2 4/2005 Tokunaga ................... 205/775
6,881,378 B1 4/2005 Zimmer ....................... 422/58
6,881,550 B2 4/2005 Phillips ....................... 435/14
6,881,551 B2 4/2005 Heller ......................... 435/14
6,881,578 B2 4/2005 Otake .......................... 436/44
6,882,940 B2 4/2005 Potts ........................... 702/23
6,884,592 B2 4/2005 Matzinger ................... 435/7.1
6,885,196 B2 4/2005 Taniike ....................... 324/444
6,885,883 B2 4/2005 Parris ......................... 600/347
6,887,239 B2 5/2005 Elstrom ....................... 606/41
6,887,253 B2 5/2005 Schraga ...................... 606/181
6,887,426 B2 5/2005 Phillips ....................... 422/56
6,887,709 B2 5/2005 Leong ........................... 436/8
6,889,069 B2 5/2005 Routt ......................... 600/319
6,890,319 B1 5/2005 Crocker ...................... 604/131
6,890,421 B2 5/2005 Ohara ..................... 205/777.5
6,890,484 B2 5/2005 Bautista ....................... 422/58
6,891,936 B2 5/2005 Kai ....................... 379/106.02
6,892,085 B2 5/2005 McIvor ....................... 600/347
6,893,396 B2 5/2005 Schulze ...................... 600/300
6,893,545 B2 5/2005 Gotoh ..................... 204/403.5
6,893,552 B1 5/2005 Wang ...................... 205/777.5
6,895,263 B2 5/2005 Shin ........................... 600/316
6,895,264 B2 5/2005 Rice ........................... 600/319
6,895,265 B2 5/2005 Silver ......................... 600/345
6,896,793 B2 5/2005 Erdosy ....................... 205/775
6,897,788 B2 5/2005 Khair ..................... 340/870.16
6,902,905 B2 6/2005 Burson ........................ 435/14
6,904,301 B2 6/2005 Raskas ....................... 600/310
6,905,733 B2 6/2005 Russel ..................... 427/393.5
6,908,008 B2 6/2005 Pugh .......................... 221/135
6,908,535 B2 6/2005 Rankin ....................... 204/406
6,908,591 B2 6/2005 MacPhee ..................... 422/22
6,908,593 B1 6/2005 Shartle ........................ 422/58
6,911,130 B2 6/2005 Brenneman ................. 204/400
6,911,131 B2 6/2005 Miyazaki ............... 204/403.14
6,911,621 B2 6/2005 Bhullar .................. 219/121.69
6,916,410 B2 7/2005 Katsuki ...................... 204/403
6,918,918 B1 7/2005 Schraga ...................... 606/182
6,922,576 B2 7/2005 Raskas ....................... 600/316
6,922,578 B2 7/2005 Eppstein ..................... 600/347
6,923,764 B2 8/2005 Aceti ......................... 600/309
6,923,894 B2 8/2005 Huang ................... 204/403.06
6,923,936 B2 8/2005 Swanson ..................... 422/22
6,924,093 B2 8/2005 Haviland ....................... 435/4
6,925,317 B1 8/2005 Samuels ..................... 600/344
6,925,393 B1 8/2005 Kalatz ......................... 702/27
6,929,649 B2 8/2005 Pugh .......................... 606/182
6,929,650 B2 8/2005 Fukuzawa ................... 606/182
6,931,327 B2 8/2005 Goode ......................... 702/22
6,931,328 B2 8/2005 Braig .......................... 702/23
6,939,310 B2 9/2005 Matzinger ................... 600/573
6,939,312 B2 9/2005 Hodges ...................... 600/583
6,939,450 B2 9/2005 Karinka ...................... 204/409
6,940,591 B2 9/2005 Sopp .......................... 356/244
6,942,518 B2 9/2005 Liamos ....................... 439/495
6,942,769 B2 9/2005 Cheng ........................ 204/400
6,942,770 B2 9/2005 Cai ....................... 204/403.04
6,944,486 B2 9/2005 Braig ......................... 600/310
6,945,943 B2 9/2005 Pugh .......................... 600/584
6,946,067 B2 9/2005 Hodges ...................... 205/792
6,946,098 B2 9/2005 Miekka ........................ 422/22
6,946,299 B2 9/2005 Neel ........................... 436/95
6,949,111 B2 9/2005 Schraga ...................... 606/182
6,949,221 B2 9/2005 Kiser .......................... 422/56
6,951,631 B1 10/2005 Catt ........................... 422/56
6,951,728 B2 10/2005 Qian ........................... 435/14
6,952,603 B2 10/2005 Gerber ....................... 600/310
6,952,604 B2 10/2005 DeNuzzio ................... 600/345
6,953,693 B2 10/2005 Neel .......................... 436/149
6,954,662 B2 10/2005 Freger ........................ 600/316
6,958,072 B2 10/2005 Schraga ...................... 606/182
6,958,129 B2 10/2005 Galen .......................... 422/57
6,958,809 B2 10/2005 Sterling ....................... 356/39
6,959,211 B2 10/2005 Rule .......................... 600/310
6,959,247 B2 10/2005 Neel ........................... 702/19
6,960,287 B2 11/2005 Charlton ..................... 205/775
6,960,289 B2 11/2005 Hodges ...................... 205/778
6,964,871 B2 11/2005 Bell ............................ 436/95
6,965,791 B1 11/2005 Hitchcock ................... 600/345
6,966,880 B2 11/2005 Boecker ..................... 600/583
6,966,977 B2 11/2005 Hasegawa ............. 204/403.07
6,967,105 B2 11/2005 Nomura ...................... 436/169
6,968,375 B1 11/2005 Brown ....................... 709/224
6,969,359 B2 11/2005 Duchon ...................... 600/583
6,969,450 B2 11/2005 Taniike ................. 204/403.01
6,969,451 B2 11/2005 Shin ........................... 204/412
6,973,706 B2 12/2005 Say ............................ 29/595
6,975,893 B2 12/2005 Say ............................ 600/347
6,977,032 B2 12/2005 Hasegawa ............. 204/403.05
6,979,544 B2 12/2005 Keen ............................. 435/6
6,979,571 B2 12/2005 Modzelewski .............. 436/164
6,982,027 B2 1/2006 Yagi ...................... 204/403.06
6,983,176 B2 1/2006 Gardner ...................... 600/310
6,983,177 B2 1/2006 Rule .......................... 600/310
6,984,307 B2 1/2006 Zweig ..................... 205/777.5
6,986,777 B2 1/2006 Kim ........................... 606/182
6,986,869 B2 1/2006 Tuohy ......................... 422/56
6,988,996 B2 1/2006 Roe ........................... 600/584
6,989,243 B2 1/2006 Yani ............................ 435/14
6,989,891 B2 1/2006 Braig .......................... 356/39
6,990,365 B1 1/2006 Parker ........................ 600/328
6,990,366 B2 1/2006 Say ............................ 600/345
6,990,367 B2 1/2006 Kiser ......................... 600/345
6,990,849 B2 1/2006 Bohm ........................ 73/53.01
6,991,918 B2 1/2006 Keith ........................... 435/31
6,991,940 B2 1/2006 Carroll ....................... 436/514
6,994,825 B2 2/2006 Haviland ...................... 422/58
6,997,317 B2 2/2006 Catelli ........................ 206/438
6,997,343 B2 2/2006 May ........................... 221/232
6,997,344 B2 2/2006 Brown ....................... 221/258
6,997,936 B2 2/2006 Marshall ..................... 606/181

6,998,247 B2 2/2006 Monfre ........................ 435/14
6,998,248 B2 2/2006 Yani ............................ 435/14
6,999,810 B2 2/2006 Berner ....................... 600/345
7,001,343 B2 2/2006 Erickson ..................... 600/573
7,001,344 B2 2/2006 Freeman ..................... 600/583
7,003,337 B2 2/2006 Harjunmaa ................. 600/316
7,003,340 B2 2/2006 Say ............................ 600/345
7,003,341 B2 2/2006 Say ............................ 600/345
7,004,928 B2 2/2006 Aceti .......................... 604/191
7,005,048 B1 2/2006 Watanabe .............. 204/403.04
7,005,273 B2 2/2006 Heller ......................... 435/25
7,005,459 B2 2/2006 Hekal ......................... 523/102
7,005,857 B2 2/2006 Stiene ........................ 324/449
7,006,857 B2 2/2006 Braig ......................... 600/310
7,006,858 B2 2/2006 Silver ......................... 600/345
7,008,384 B2 3/2006 Tapper ....................... 600/573
7,010,432 B2 3/2006 Kermani ...................... 702/19
7,011,630 B2 3/2006 Desai ......................... 600/309
7,011,954 B2 3/2006 Ouyang ...................... 435/7.9
7,014,615 B2 3/2006 Erickson ..................... 600/573
7,015,262 B2 3/2006 Leong ........................ 523/205
7,016,713 B2 3/2006 Gardner ...................... 600/310
7,018,568 B2 3/2006 Tierney ...................... 252/511
7,018,848 B2 3/2006 Douglas ..................... 436/524
7,022,217 B2 4/2006 Hodges .................... 205/777.5
7,022,218 B2 4/2006 Taniike .................... 205/777.5
7,022,286 B2 4/2006 Lemke ........................ 422/67
7,024,236 B2 4/2006 Ford .......................... 600/345
7,024,248 B2 4/2006 Penner ........................ 607/60
7,024,399 B2 4/2006 Sumner ....................... 706/45
7,025,425 B2 4/2006 Kovatchev .................. 300/365
7,025,774 B2 4/2006 Freeman ..................... 606/181
7,027,848 B2 4/2006 Robinson .................... 600/310
7,029,444 B2 4/2006 Shin .......................... 600/365
7,033,322 B2 4/2006 Silver ......................... 600/486
7,033,371 B2 4/2006 Alden ......................... 606/181
7,039,560 B2 5/2006 Kawatahara ................ 702/187
7,041,057 B1 5/2006 Faupel ....................... 600/365
7,041,063 B2 5/2006 Abreu ........................ 600/549
7,041,068 B2 5/2006 Freeman ..................... 600/583
7,041,254 B2 5/2006 Haviland ..................... 422/58
7,041,468 B2 5/2006 Drucker ....................... 435/14
7,043,287 B1 5/2006 Khalil ......................... 600/310
7,044,911 B2 5/2006 Drinan ....................... 600/300
7,045,054 B1 5/2006 Buck .......................... 205/778
7,045,097 B2 5/2006 Kovacs .................... 422/82.08
7,045,310 B2 5/2006 Buck ......................... 435/7.93
7,045,361 B2 5/2006 Heiss ......................... 436/172
7,047,070 B2 5/2006 Wilkinson ................... 604/20
7,047,795 B2 5/2006 Sato .......................... 73/64.56
7,049,130 B2 5/2006 Carroll ................... 435/287.2
7,050,843 B2 5/2006 Shartle ....................... 600/345
7,051,495 B2 5/2006 Lang ........................... 53/475
7,052,268 B2 5/2006 Powell ....................... 425/542
7,052,591 B2 5/2006 Gao ........................... 204/490
7,052,652 B2 5/2006 Zanzucchi ............... 422/82.05
7,052,864 B2 5/2006 Durkop ....................... 435/25
7,054,682 B2 5/2006 Young ......................... 604/20
7,054,759 B2 5/2006 Fukunaga .................... 702/23
D523,555 S 6/2006 Loerwald ................... D24/146
7,056,425 B2 6/2006 Hasegawa .............. 204/403.04
7,056,495 B2 6/2006 Roser .......................... 424/45
7,058,437 B2 6/2006 Buse .......................... 600/347
7,060,059 B2 6/2006 Keith ......................... 604/504
7,060,192 B2 6/2006 Yuzhakov .................... 216/11
7,061,593 B2 6/2006 Braig .......................... 356/39
7,063,234 B2 6/2006 Giraud ....................... 221/271
7,063,774 B2 6/2006 Bhullar .................. 204/403.02
7,063,775 B2 6/2006 Yamaoka ............... 204/403.06
7,063,776 B2 6/2006 Huang ................... 204/403.14
7,066,884 B2 6/2006 Custer ........................ 600/309
7,066,885 B2 6/2006 Erickson ..................... 600/309
7,070,564 B2 7/2006 Matzinger ................... 600/300
7,070,680 B2 7/2006 Bae ....................... 204/403.04
7,073,246 B2 7/2006 Bhullar ........................ 29/595
7,074,307 B2 7/2006 Simpson ................ 204/403.04
7,074,308 B2 7/2006 Mao ...................... 204/403.14
7,077,328 B2 7/2006 Krishnaswamy ....... 235/472.01
7,077,828 B2 7/2006 Kuhr .......................... 604/207
7,078,480 B2 7/2006 Nagel ......................... 530/322
7,081,188 B1 7/2006 Cho ...................... 204/403.04
7,083,712 B2 8/2006 Morita ....................... 205/775
7,086,277 B2 8/2006 Tess .......................... 73/53.01
7,087,149 B1 8/2006 Muguruma ................. 205/778
7,090,764 B2 8/2006 Iyengar ...................... 205/775
7,096,053 B2 8/2006 Loeb .......................... 600/317
7,096,124 B2 8/2006 Sterling ....................... 702/23
7,097,631 B2 8/2006 Trautman .................... 604/46
7,098,038 B2 8/2006 Fukuoka ..................... 436/164
7,103,578 B2 9/2006 Beck ........................... 705/75
7,105,066 B2 9/2006 Schraga ...................... 606/182
7,107,253 B1 9/2006 Sumner ....................... 706/45
7,108,680 B2 9/2006 Rohr .......................... 604/151
7,108,778 B2 9/2006 Simpson ..................... 205/778
7,109,271 B2 9/2006 Liu ............................ 525/283
7,110,112 B2 9/2006 Uchida ....................... 356/364
7,110,803 B2 9/2006 Shults ........................ 600/347
7,112,265 B1 9/2006 McAleer ............... 204/403.09
7,112,451 B2 9/2006 Takahashi ................... 436/514
7,115,362 B2 10/2006 Douglas ........................ 435/4
7,118,351 B2 10/2006 Effenhauser ................ 417/208
7,118,667 B2 10/2006 Lee ......................... 205/777.5
7,118,668 B1 10/2006 Edelbrock ................ 205/777.5
7,118,916 B2 10/2006 Matzinger .................... 436/34
7,118,919 B2 10/2006 Yatscoff ....................... 436/56
7,120,483 B2 10/2006 Russell ....................... 600/345
7,122,102 B2 10/2006 Wogoman ................... 204/400
7,122,110 B2 10/2006 Deng ...................... 205/777.5
7,122,111 B2 10/2006 Tokunaga ................... 205/792
7,125,481 B2 10/2006 Musho ....................... 205/775
7,129,038 B2 10/2006 Gopalan ........................ 435/4
RE39,390 E 11/2006 Hasegawa .............. 204/403.09
D531,725 S 11/2006 Loerwald ................... D24/146
7,131,342 B2 11/2006 Hodges .................. 73/864.72
7,131,984 B2 11/2006 Sato ........................... 606/182
7,132,041 B2 11/2006 Deng ...................... 205/777.5
7,133,710 B2 11/2006 Acosta ....................... 600/316
7,134,999 B2 11/2006 Brauker ...................... 600/309
7,135,100 B1 11/2006 Lau ....................... 204/403.14
7,137,957 B2 11/2006 Erickson ..................... 600/573
7,138,041 B2 11/2006 Su ........................ 204/403.04
7,138,089 B2 11/2006 Aitken .................... 422/82.01
7,141,058 B2 11/2006 Briggs ........................ 606/181
7,144,404 B2 12/2006 Whitson ..................... 606/181
7,144,485 B2 12/2006 Hsu ...................... 204/403.02
7,144,495 B2 12/2006 Teodorezyk ................ 205/792
7,144,496 B2 12/2006 Meserol ...................... 205/792
7,147,825 B2 12/2006 Matsuda ....................... 422/58
7,150,755 B2 12/2006 Levaughn ................... 606/181
7,150,975 B2 12/2006 Tamada ........................ 435/14
7,150,995 B2 12/2006 Xie ............................. 436/67
7,153,696 B2 12/2006 Fukuoka ..................... 436/164
7,155,371 B2 12/2006 Kawatahara ................ 702/187
7,160,251 B2 1/2007 Neel .......................... 600/365
7,160,313 B2 1/2007 Galloway ................... 606/167
7,163,616 B2 1/2007 Vreeke .................... 205/777.5
7,166,074 B2 1/2007 Reghabi ..................... 600/365
7,167,734 B2 1/2007 Khalil ......................... 600/310
7,167,818 B2 1/2007 Brown ......................... 703/11
2001/0011157 A1 8/2001 Latterell ..................... 600/576
2001/0016682 A1 8/2001 Berner ....................... 600/345
2001/0017269 A1 8/2001 Heller ..................... 205/777.5
2001/0027328 A1 10/2001 Lum .......................... 606/186
2001/0054319 A1 12/2001 Heller ......................... 73/849
2002/0016606 A1 2/2002 Moerman ................... 606/181
2002/0019748 A1 2/2002 Brown ........................... 705/2

2002/0025469 A1 2/2002 Heller ........................ 429/43
2002/0029058 A1 3/2002 Levaughn .................. 606/181
2002/0040230 A1 4/2002 Kuhr .......................... 606/181
2002/0042090 A1 4/2002 Heller ........................ 435/14
2002/0044890 A1 4/2002 Black .......................... 422/56
2002/0052618 A1 5/2002 Haar .......................... 606/181
2002/0053523 A1 5/2002 Liamos ...................... 205/787
2002/0057993 A1 5/2002 Maisey .................. 422/82.01
2002/0076349 A1 6/2002 Aitken ........................ 422/58
2002/0078091 A1 6/2002 Vu ............................ 707/513
2002/0081559 A1 6/2002 Brown .................. 434/307 R
2002/0081588 A1 6/2002 Lumley-Woodyear ......... 435/6
2002/0084196 A1 7/2002 Liamos ...................... 205/792
2002/0087056 A1 7/2002 Aceti
2002/0092612 A1 7/2002 Davies ...................... 156/292
2002/0120216 A1 8/2002 Fritz .......................... 600/583
2002/0120261 A1 8/2002 Morris ........................ 606/41
2002/0130042 A1 9/2002 Moerman ............. 204/403.01
2002/0133377 A1 9/2002 Brown .......................... 705/3
2002/0136667 A1 9/2002 Subramanian ............. 422/100
2002/0136863 A1 9/2002 Subramanian ............. 428/156
2002/0137998 A1 9/2002 Smart ........................ 600/347
2002/0138040 A1 9/2002 Flora .......................... 604/116
2002/0148739 A2 10/2002 Liamos ...................... 205/787
2002/0160520 A1 10/2002 Orloff ........................ 436/72
2002/0161289 A1 10/2002 Hopkins .................... 600/322
2002/0168290 A1 11/2002 Yuzhakov ................... 422/56
2002/0176984 A1 11/2002 Smart ........................ 428/336
2002/0177761 A1 11/2002 Orloff ........................ 600/309
2002/0188224 A1 12/2002 Roe .......................... 600/584
2003/0018282 A1 1/2003 Effenhauser ............... 600/583
2003/0018300 A1 1/2003 Duchon ................ 604/164.01
2003/0028125 A1 2/2003 Yuzhakov
2003/0028126 A1 2/2003 List ........................... 600/583
2003/0050537 A1 3/2003 Wessel ...................... 600/300
2003/0050573 A1 3/2003 Kuhr .......................... 600/567
2003/0050656 A1 3/2003 Schraga ..................... 606/182
2003/0060730 A1 3/2003 Perez ........................ 600/576
2003/0069753 A1 4/2003 Brown .......................... 705/2
2003/0073089 A1 4/2003 Mauze .......................... 435/6
2003/0073229 A1 4/2003 Greenstein .............. 435/287.2
2003/0073931 A1 4/2003 Boecker .................... 600/573
2003/0083685 A1 5/2003 Freeman .................... 606/181
2003/0083686 A1 5/2003 Freeman .................... 606/181
2003/0088160 A1 5/2003 Halleck ...................... 600/300
2003/0088191 A1 5/2003 Freeman et al. ........... 600/583
2003/0089730 A1 5/2003 May .......................... 221/232
2003/0093010 A1 5/2003 Essenpreis ................. 600/583
2003/0100040 A1 5/2003 Bonnecaze .................. 435/14
2003/0106810 A1 6/2003 Douglas ................. 205/777.5
2003/0109777 A1 6/2003 Kloepfer .................... 600/367
2003/0111357 A1 6/2003 Black ........................ 205/775
2003/0113827 A1 6/2003 Burkoth ...................... 435/14
2003/0116447 A1 6/2003 Sturridge ................ 205/777.5
2003/0135333 A1 7/2003 Aceti .......................... 702/31
2003/0139653 A1 7/2003 Manser ...................... 600/300
2003/0143113 A2 7/2003 Yuzhakov ................... 422/56
2003/0144608 A1 7/2003 Kojima ...................... 600/583
2003/0144609 A1 7/2003 Kennedy .................... 600/583
2003/0146110 A1 8/2003 Karinka .................. 205/777.5
2003/0149348 A1 8/2003 Raskas ...................... 600/310
2003/0149377 A1 8/2003 Erickson .................... 600/573
2003/0153900 A1 8/2003 Aceti ...................... 604/890.1
2003/0159944 A1 8/2003 Pottgen .................. 205/777.5
2003/0163351 A1 8/2003 Brown .......................... 705/2
2003/0178322 A1 9/2003 Iyengar ...................... 205/775
2003/0191415 A1 10/2003 Moerman .................. 600/584
2003/0195435 A1 10/2003 Williams ................... 600/583
2003/0195540 A1 10/2003 Moerman .................. 606/181
2003/0199744 A1 10/2003 Buse .......................... 600/347
2003/0199789 A1 10/2003 Boecker .................... 600/575
2003/0199790 A1 10/2003 Boecker .................... 600/576
2003/0199791 A1 10/2003 Boecker .................... 600/576
2003/0199891 A1 10/2003 Argauer ..................... 606/181
2003/0199893 A1 10/2003 Boecker .................... 606/181
2003/0199894 A1 10/2003 Boecker .................... 606/181
2003/0199895 A1 10/2003 Boecker .................... 606/181
2003/0199896 A1 10/2003 Boecker .................... 606/181
2003/0199897 A1 10/2003 Boecker .................... 606/181
2003/0199898 A1 10/2003 Boecker .................... 606/181
2003/0199899 A1 10/2003 Boecker .................... 606/181
2003/0199900 A1 10/2003 Boecker .................... 606/181
2003/0199901 A1 10/2003 Boecker .................... 606/181
2003/0199902 A1 10/2003 Boecker .................... 606/181
2003/0199903 A1 10/2003 Boecker .................... 606/181
2003/0199904 A1 10/2003 Boecker .................... 606/181
2003/0199905 A1 10/2003 Boecker .................... 606/181
2003/0199906 A1 10/2003 Boecker .................... 606/181
2003/0199907 A1 10/2003 Boecker .................... 606/181
2003/0199908 A1 10/2003 Boecker .................... 606/181
2003/0199909 A1 10/2003 Boecker .................... 606/181
2003/0199910 A1 10/2003 Boecker .................... 606/181
2003/0199911 A1 10/2003 Boecker .................... 606/181
2003/0199912 A1 10/2003 Pugh .......................... 606/182
2003/0201194 A1 10/2003 Heller .................... 205/777.5
2003/0203352 A1 10/2003 Haviland ...................... 435/4
2003/0206828 A1 11/2003 Bell ............................ 422/44
2003/0208140 A1 11/2003 Pugh .......................... 600/584
2003/0212344 A1 11/2003 Yuzhakov .................. 600/583
2003/0212345 A1 11/2003 McAllister ................. 600/584
2003/0212346 A1 11/2003 McAllister ................. 600/584
2003/0212347 A1 11/2003 Sohrab ...................... 600/584
2003/0212423 A1 11/2003 Pugh .......................... 606/181
2003/0212424 A1 11/2003 Briggs ....................... 606/181
2003/0212579 A1 11/2003 Brown .......................... 705/2
2003/0216767 A1 11/2003 List ........................... 606/181
2003/0217918 A1 11/2003 Davies ................. 204/403.14
2003/0220552 A1 11/2003 Reghabi .................... 600/365
2003/0220663 A1 11/2003 Fletcher ..................... 606/182
2003/0223906 A1 12/2003 McAllister ................... 422/58
2003/0225317 A1 12/2003 Schell ....................... 600/300
2003/0225429 A1 12/2003 Garthe ...................... 606/182
2003/0225430 A1 12/2003 Schraga ..................... 606/182
2003/0228637 A1 12/2003 Wang ........................ 435/7.9
2003/0229514 A2 12/2003 Brown .......................... 705/2
2003/0232370 A1 12/2003 Trifiro .......................... 435/6
2003/0233055 A1 12/2003 Erickson .................... 600/573
2003/0233112 A1 12/2003 Alden et al. ............... 606/181
2003/0233113 A1 12/2003 Alden et al. ............... 606/182
2004/0006285 A1 1/2004 Douglas .................... 600/583
2004/0007585 A1 1/2004 Griffith ...................... 221/232
2004/0009100 A1 1/2004 Simons ..................... 422/102
2004/0010279 A1 1/2004 Freeman .................... 606/182
2004/0015064 A1 1/2004 Parsons .................... 600/347
2004/0019250 A1 1/2004 Catelli .......................... 600/1
2004/0019259 A1 1/2004 Brown ....................... 600/300
2004/0026243 A1 2/2004 Davies ................. 204/403.14
2004/0030353 A1 2/2004 Schmelzeisen ............. 606/201
2004/0031682 A1 2/2004 Wilsey ................... 204/403.1
2004/0034318 A1 2/2004 Fritz ............................ 604/19
2004/0038045 A1 2/2004 Smart ........................ 428/446
2004/0039303 A1 2/2004 Wurster ..................... 600/584
2004/0039342 A1 2/2004 Eppstein .................... 604/200
2004/0039407 A1 2/2004 Schraga ..................... 606/181
2004/0039408 A1 2/2004 Abulhaj ..................... 606/181
2004/0049219 A1 3/2004 Briggs ....................... 606/181
2004/0049220 A1 3/2004 Boecker .................... 606/181
2004/0050694 A1 3/2004 Yang .................... 204/403.02
2004/0054267 A1 3/2004 Feldman .................... 600/316
2004/0054898 A1 3/2004 Heller .................... 205/777.5
2004/0059256 A1 3/2004 Perez ........................ 600/583
2004/0060818 A1 4/2004 Feldman ............... 204/403.01
2004/0061841 A1 4/2004 Black .......................... 355/30
2004/0064068 A1 4/2004 DeNuzzio .................. 600/583
2004/0087990 A1 5/2004 Boecker .................... 606/181
2004/0092842 A1 5/2004 Boecker .................... 600/575

| | | | | |
|---|---|---|---|---|
| 2004/0092994 | A1 | 5/2004 | Briggs | 606/181 |
| 2004/0092995 | A1 | 5/2004 | Boecker | 606/181 |
| 2004/0096991 | A1 | 5/2004 | Zhang | 436/518 |
| 2004/0098009 | A1 | 5/2004 | Boecker | 606/181 |
| 2004/0098010 | A1 | 5/2004 | Davison | 606/181 |
| 2004/0102803 | A1 | 5/2004 | Boecker | 606/183 |
| 2004/0106855 | A1 | 6/2004 | Brown | 600/301 |
| 2004/0106858 | A1 | 6/2004 | Say | 600/345 |
| 2004/0106859 | A1 | 6/2004 | Say | 600/345 |
| 2004/0106860 | A1 | 6/2004 | Say | 600/345 |
| 2004/0106904 | A1 | 6/2004 | Gonnelli | 604/173 |
| 2004/0106941 | A1 | 6/2004 | Roe | 606/181 |
| 2004/0107116 | A1 | 6/2004 | Brown | 705/2 |
| 2004/0115754 | A1 | 6/2004 | Chang | 435/14 |
| 2004/0115831 | A1 | 6/2004 | Meathrel | 436/514 |
| 2004/0116780 | A1 | 6/2004 | Brown | 600/300 |
| 2004/0116829 | A1 | 6/2004 | Raney | 600/573 |
| 2004/0117207 | A1 | 6/2004 | Brown | 705/2 |
| 2004/0117208 | A1 | 6/2004 | Brown | 705/2 |
| 2004/0117209 | A1 | 6/2004 | Brown | 705/2 |
| 2004/0117210 | A1 | 6/2004 | Brown | 705/2 |
| 2004/0122339 | A1 | 6/2004 | Roe | |
| 2004/0127818 | A1 | 7/2004 | Roe | 600/583 |
| 2004/0127819 | A1 | 7/2004 | Roe | 600/583 |
| 2004/0127928 | A1 | 7/2004 | Whitson | 606/181 |
| 2004/0127929 | A1 | 7/2004 | Roe | 606/181 |
| 2004/0132167 | A1 | 7/2004 | Rule | 435/287.1 |
| 2004/0133125 | A1 | 7/2004 | Miyashita | 600/573 |
| 2004/0133127 | A1 | 7/2004 | Roe | 600/583 |
| 2004/0137640 | A1 | 7/2004 | Hirao | 436/514 |
| 2004/0138541 | A1 | 7/2004 | Ward | 600/345 |
| 2004/0138588 | A1 | 7/2004 | Saikley | 600/583 |
| 2004/0138688 | A1 | 7/2004 | Giraud | 606/181 |
| 2004/0146958 | A1 | 7/2004 | Bae | 435/14 |
| 2004/0154932 | A1 | 8/2004 | Deng | 205/777.5 |
| 2004/0157017 | A1 | 8/2004 | Mauze | 428/35.7 |
| 2004/0157149 | A1 | 8/2004 | Hofmann | 430/131 |
| 2004/0157319 | A1 | 8/2004 | Keen | 435/287.2 |
| 2004/0157338 | A1 | 8/2004 | Burke | 436/147 |
| 2004/0157339 | A1 | 8/2004 | Burke | 436/149 |
| 2004/0158137 | A1 | 8/2004 | Eppstein | 600/347 |
| 2004/0158271 | A1 | 8/2004 | Hamamoto | 606/181 |
| 2004/0161737 | A1 | 8/2004 | Yang | 435/5 |
| 2004/0162473 | A1 | 8/2004 | Sohrab | 600/345 |
| 2004/0162474 | A1 | 8/2004 | Kiser | 600/345 |
| 2004/0162506 | A1 | 8/2004 | Duchon | 600/583 |
| 2004/0162573 | A1 | 8/2004 | Keheiri | 606/182 |
| 2004/0167383 | A1 | 8/2004 | Kim | 600/365 |
| 2004/0171057 | A1 | 9/2004 | Yang | 435/6 |
| 2004/0171968 | A1 | 9/2004 | Katsuki | 600/583 |
| 2004/0172000 | A1 | 9/2004 | Roe | 604/361 |
| 2004/0173472 | A1 | 9/2004 | Jung | 205/777.5 |
| 2004/0173488 | A1 | 9/2004 | Griffin | 206/363 |
| 2004/0176705 | A1 | 9/2004 | Stevens | 600/584 |
| 2004/0176732 | A1 | 9/2004 | Frazier | 604/345 |
| 2004/0178066 | A1 | 9/2004 | Miyazaki | 204/403.01 |
| 2004/0178067 | A1 | 9/2004 | Miyazaki | 204/403.1 |
| 2004/0178216 | A1 | 9/2004 | Brickwood | 221/268 |
| 2004/0180379 | A1 | 9/2004 | van Duyne | 435/7.1 |
| 2004/0182703 | A1 | 9/2004 | Bell | 204/403.11 |
| 2004/0185568 | A1 | 9/2004 | Matsumoto | 436/8 |
| 2004/0186359 | A1 | 9/2004 | Beaudoin | 600/310 |
| 2004/0186394 | A1 | 9/2004 | Roe | 600/598 |
| 2004/0186500 | A1 | 9/2004 | Koilke | 606/181 |
| 2004/0193201 | A1 | 9/2004 | Kim | 606/181 |
| 2004/0193377 | A1 | 9/2004 | Brown | 702/19 |
| 2004/0194302 | A1 | 10/2004 | Bhullar | 29/847 |
| 2004/0197231 | A1 | 10/2004 | Katsuki | 422/68.1 |
| 2004/0197821 | A1 | 10/2004 | Bauer | 437/7.1 |
| 2004/0199062 | A1 | 10/2004 | Pettersson | 600/316 |
| 2004/0199409 | A1 | 10/2004 | Brown | 705/3 |
| 2004/0200720 | A1 | 10/2004 | Musho | 204/403.01 |
| 2004/0200721 | A1 | 10/2004 | Bhullar | 204/403.01 |
| 2004/0202576 | A1 | 10/2004 | Aceti | 422/82.05 |
| 2004/0204662 | A1 | 10/2004 | Perez | 600/583 |
| 2004/0206625 | A1 | 10/2004 | Bhullar | 204/403.1 |
| 2004/0206636 | A1 | 10/2004 | Hodges | 205/792 |
| 2004/0206658 | A1 | 10/2004 | Hammerstedt | 206/524.1 |
| 2004/0209307 | A1 | 10/2004 | Valkirs | 435/7.1 |
| 2004/0209350 | A1 | 10/2004 | Sakata | 435/287.1 |
| 2004/0209354 | A1 | 10/2004 | Mathies | 435/287.2 |
| 2004/0210279 | A1 | 10/2004 | Gruzdev | 607/89 |
| 2004/0211666 | A1 | 10/2004 | Pamidi | 204/403.01 |
| 2004/0214253 | A1 | 10/2004 | Paek | 435/7.92 |
| 2004/0215224 | A1 | 10/2004 | Sakata | 606/181 |
| 2004/0215225 | A1 | 10/2004 | Nakayama | 606/182 |
| 2004/0216516 | A1 | 11/2004 | Sato | 73/64.56 |
| 2004/0217019 | A1 | 11/2004 | Cai | 205/792 |
| 2004/0219500 | A1 | 11/2004 | Brown | 434/307 R |
| 2004/0219535 | A1 | 11/2004 | Bell | 435/6 |
| 2004/0220456 | A1 | 11/2004 | Eppstein | 600/309 |
| 2004/0220495 | A1 | 11/2004 | Cahir | 600/562 |
| 2004/0220564 | A1 | 11/2004 | Ho | 606/47 |
| 2004/0220603 | A1 | 11/2004 | Rutynowski | 606/181 |
| 2004/0222092 | A1 | 11/2004 | Musho | 204/401 |
| 2004/0224369 | A1 | 11/2004 | Cai | 435/7.7 |
| 2004/0225230 | A1 | 11/2004 | Liamos | 600/583 |
| 2004/0225311 | A1 | 11/2004 | Levaughn | 606/181 |
| 2004/0225312 | A1 | 11/2004 | Orloff | 606/182 |
| 2004/0230216 | A1 | 11/2004 | Levaughn | 606/181 |
| 2004/0231984 | A1 | 11/2004 | Lauks | 204/416 |
| 2004/0232009 | A1 | 11/2004 | Okuda | 205/789 |
| 2004/0236250 | A1 | 11/2004 | Hodges | 600/583 |
| 2004/0236251 | A1 | 11/2004 | Roe | 600/583 |
| 2004/0236268 | A1 | 11/2004 | Mitragotri | 604/20 |
| 2004/0236362 | A1 | 11/2004 | Schraga | 606/181 |
| 2004/0238357 | A1 | 12/2004 | Bhullar | 204/400 |
| 2004/0238358 | A1 | 12/2004 | Forrow | 204/403 |
| 2004/0238359 | A1 | 12/2004 | Ikeda | 204/403.1 |
| 2004/0241746 | A1 | 12/2004 | Adlassnig | 435/7.1 |
| 2004/0242977 | A1 | 12/2004 | Dosmann | 600/315 |
| 2004/0243164 | A1 | 12/2004 | D'Agostino | 606/181 |
| 2004/0243165 | A1 | 12/2004 | Koike | 606/181 |
| 2004/0245101 | A1 | 12/2004 | Willner | 204/403 |
| 2004/0248282 | A1 | 12/2004 | Sobha | 435/287.2 |
| 2004/0248312 | A1 | 12/2004 | Vreeke | 436/95 |
| 2004/0249254 | A1 | 12/2004 | Racchini | 600/347 |
| 2004/0249310 | A1 | 12/2004 | Shartle | 600/583 |
| 2004/0249311 | A1 | 12/2004 | Haar | 600/584 |
| 2004/0249405 | A1 | 12/2004 | Watanabe | 606/181 |
| 2004/0249406 | A1 | 12/2004 | Griffin | 606/182 |
| 2004/0251131 | A1 | 12/2004 | Ueno | 204/403 |
| 2004/0253634 | A1 | 12/2004 | Wang | 435/7.1 |
| 2004/0254434 | A1 | 12/2004 | Goodnow | 600/365 |
| 2004/0254599 | A1 | 12/2004 | Lipoma | 606/181 |
| 2004/0256228 | A1 | 12/2004 | Huang | 204/434 |
| 2004/0256248 | A1 | 12/2004 | Burke | 205/792 |
| 2004/0256685 | A1 | 12/2004 | Chou | 257/414 |
| 2004/0258564 | A1 | 12/2004 | Charlton | 422/58 |
| 2004/0260204 | A1 | 12/2004 | Boecker | 600/584 |
| 2004/0260324 | A1 | 12/2004 | Fukuzawa | 606/181 |
| 2004/0260325 | A1 | 12/2004 | Kuhr | 606/181 |
| 2004/0260326 | A1 | 12/2004 | Lipoma | 606/182 |
| 2004/0260511 | A1 | 12/2004 | Burke | 702/182 |
| 2004/0267105 | A1 | 12/2004 | Monfre | 600/344 |
| 2004/0267160 | A9 | 12/2004 | Perez | 600/583 |
| 2004/0267229 | A1 | 12/2004 | Moerman | 604/500 |
| 2004/0267299 | A1 | 12/2004 | Kuriger | 606/181 |
| 2004/0267300 | A1 | 12/2004 | Mace | 606/182 |
| 2005/0000806 | A1 | 1/2005 | Hsieh | 203/403.1 |
| 2005/0000807 | A1 | 1/2005 | Wang | 204/403.81 |
| 2005/0000808 | A1 | 1/2005 | Cui | 203/403.14 |
| 2005/0003470 | A1 | 1/2005 | Nelson | 435/14 |
| 2005/0004437 | A1 | 1/2005 | Kaufmann | 600/300 |
| 2005/0004494 | A1 | 1/2005 | Perez | 600/583 |
| 2005/0008537 | A1 | 1/2005 | Mosolu | 422/56 |

2005/0008851 A1 1/2005 Ezoe ......................... 428/336
2005/0009191 A1 1/2005 Swenson .................... 436/43
2005/0010090 A1 1/2005 Acosta ...................... 600/316
2005/0010093 A1 1/2005 Ford ......................... 600/345
2005/0010134 A1 1/2005 Douglas .................... 600/573
2005/0010137 A1 1/2005 Hodges ..................... 600/583
2005/0010198 A1 1/2005 Marchitto ..................... 606/9
2005/0011759 A1 1/2005 Moerman ............. 204/403.03
2005/0013731 A1 1/2005 Burke ......................... 422/56
2005/0014997 A1 1/2005 Ruchti ....................... 600/310
2005/0015020 A1 1/2005 Levaughn .................. 600/583
2005/0016844 A1 1/2005 Burke .................... 204/403.1
2005/0019212 A1 1/2005 Bhullar ....................... 422/56
2005/0019219 A1 1/2005 Oshiman ................ 422/82.12
2005/0019805 A1 1/2005 Groll ............................ 435/6
2005/0019945 A1 1/2005 Groll ......................... 436/169
2005/0019953 A1 1/2005 Groll ......................... 436/514
2005/0021066 A1 1/2005 Kuhr ......................... 606/181
2005/0027211 A1 2/2005 Kuhr ......................... 600/583
2005/0027562 A1 2/2005 Brown ......................... 705/2
2005/0033341 A1 2/2005 Vreeke ...................... 606/181
2005/0034983 A1 2/2005 Chambers ............. 204/403.01
2005/0036020 A1 2/2005 Li ............................. 347/100
2005/0036146 A1 2/2005 Braig ........................ 356/246
2005/0036906 A1 2/2005 Katsuji ........................ 422/58
2005/0036909 A1 2/2005 Erickson ..................... 422/61
2005/0037482 A1 2/2005 Braig ........................ 435/287
2005/0038329 A1 2/2005 Morris ...................... 600/319
2005/0038330 A1 2/2005 Jansen ...................... 600/345
2005/0038463 A1 2/2005 Davar ....................... 606/181
2005/0038464 A1 2/2005 Schraga ..................... 606/182
2005/0038465 A1 2/2005 Schraga ..................... 606/182
2005/0038674 A1 2/2005 Braig ........................... 705/2
2005/0042766 A1 2/2005 Ohman ...................... 436/174
2005/0043894 A1 2/2005 Fernandez .................. 702/19
2005/0043965 A1 2/2005 Heller .......................... 705/2
2005/0045476 A1 3/2005 Neel ...................... 204/403.2
2005/0049473 A1 3/2005 Desai ........................ 600/347
2005/0050859 A1 3/2005 Coppeta ...................... 53/471
2005/0054082 A1 3/2005 Pachl ..................... 435/287.2
2005/0059895 A1 3/2005 Brown ...................... 600/481
2005/0060194 A1 3/2005 Brown ......................... 705/2
2005/0067280 A1 3/2005 Reid .................... 204/403.14
2005/0067737 A1 3/2005 Rappin ................. 264/272.19
2005/0070771 A1 3/2005 Rule ......................... 600/316
2005/0070819 A1 3/2005 Poux ......................... 600/576
2005/0070945 A1 3/2005 Schraga ..................... 606/182
2005/0072670 A1 4/2005 Hasegawa ............. 204/403.01
2005/0077176 A1 4/2005 Hodges ................ 204/403.01
2005/0077584 A1 4/2005 Uhland ...................... 257/414
2005/0079542 A1 4/2005 Cullen ....................... 435/7.1
2005/0080652 A1 4/2005 Brown ......................... 705/2
2005/0085839 A1 4/2005 Allen ........................ 606/181
2005/0085840 A1 4/2005 Yi ............................. 606/182
2005/0086083 A1 4/2005 Brown ......................... 705/2
2005/0090754 A1 4/2005 Wolf ......................... 600/509
2005/0090850 A1 4/2005 Toes .......................... 606/182
2005/0096520 A1 5/2005 Maekawa .................. 600/365
2005/0096565 A1 5/2005 Chang ....................... 600/584
2005/0096586 A1 5/2005 Trautman ................... 604/46
2005/0096587 A1 5/2005 Santini ....................... 604/66
2005/0096686 A1 5/2005 Allen ........................ 606/181
2005/0098431 A1 5/2005 Hodges ................ 204/403.01
2005/0098432 A1 5/2005 Grundel .................. 204/403.2
2005/0098433 A1 5/2005 Grundel .................. 204/403.2
2005/0098434 A1 5/2005 Grundel ................ 204/403.02
2005/0100880 A1 5/2005 Chang .......................... 435/4
2005/0101841 A9 5/2005 Kaylor ...................... 600/300
2005/0101979 A1 5/2005 Alden ....................... 606/181
2005/0101980 A1 5/2005 Alden ....................... 606/181
2005/0101981 A1 5/2005 Alden ....................... 606/181
2005/0103624 A1 5/2005 Bhullar ................. 204/403.01
2005/0106713 A1 5/2005 Phan ...................... 435/287.2
2005/0109637 A1 5/2005 Iyengar ..................... 205/775
2005/0112782 A1 5/2005 Buechler ................... 436/518
2005/0113658 A1 5/2005 Jacobson ................... 600/342
2005/0113717 A1 5/2005 Matzinger .................. 600/573
2005/0114062 A1 5/2005 Davies ...................... 702/104
2005/0114154 A1 5/2005 Wolkowiez ................... 705/1
2005/0114444 A1 5/2005 Brown ...................... 709/203
2005/0118056 A1 6/2005 Swanson ..................... 423/23
2005/0119681 A1 6/2005 Marshall .................... 606/181
2005/0123443 A1 6/2005 Fujiwara ...................... 422/58
2005/0123680 A1 6/2005 Kang ..................... 427/248.1
2005/0124869 A1 6/2005 Hefti ......................... 600/316
2005/0125017 A1 6/2005 Kudrna ...................... 606/181
2005/0125018 A1 6/2005 Galloway .................. 606/181
2005/0125019 A1 6/2005 Kudrna ...................... 606/182
2005/0126929 A1 6/2005 Mansouri ................... 205/778
2005/0130248 A1 6/2005 Willner ....................... 435/14
2005/0130249 A1 6/2005 Parris ......................... 435/14
2005/0130292 A1 6/2005 Ahn ....................... 435/287.1
2005/0131286 A1 6/2005 Parker ....................... 600/328
2005/0131441 A1 6/2005 Iio ............................ 606/182
2005/0133368 A1 6/2005 Davies ................. 204/403.01
2005/0136471 A1 6/2005 Bhullar .......................... 435/6
2005/0136501 A1 6/2005 Kuriger ....................... 435/14
2005/0136529 A1 6/2005 Yang ......................... 435/287
2005/0136550 A1 6/2005 Yang ......................... 436/514
2005/0137531 A1 6/2005 Gonnelli .................... 604/173
2005/0137536 A1 6/2005 Gonnelli .................... 604/264
2005/0143675 A1 6/2005 Neel ......................... 600/583
2005/0143713 A1 6/2005 Delmore .................... 604/506
2005/0143771 A1 6/2005 Stout ......................... 606/181
2005/0145490 A1 7/2005 Shinno ...................... 204/403
2005/0145491 A1 7/2005 Amano ...................... 204/403
2005/0145520 A1 7/2005 Ilo ............................ 206/365
2005/0149088 A1 7/2005 Fukuda ...................... 606/181
2005/0149089 A1 7/2005 Trissel ....................... 606/181
2005/0150762 A1 7/2005 Butters ...................... 204/403
2005/0150763 A1 7/2005 Butters ...................... 204/403
2005/0154277 A1 7/2005 Ting .......................... 600/407
2005/0154374 A1 7/2005 Hunter ...................... 604/890
2005/0154410 A1 7/2005 Conway .................... 606/181
2005/0154616 A1 7/2005 Iliff ............................... 705/3
2005/0158850 A1 7/2005 Kubo ..................... 435/287.2
2005/0159656 A1 7/2005 Hockersmith ............... 600/315
2005/0159768 A1 7/2005 Boehm ...................... 606/182
2005/0164322 A1 7/2005 Heller ......................... 435/14
2005/0164329 A1 7/2005 Wallace-Davis ............ 435/25
2005/0165285 A1 7/2005 Iliff ........................... 600/300
2005/0165393 A1 7/2005 Eppstein ...................... 606/41
2005/0165622 A1 7/2005 Neel ............................ 705/2
2005/0169961 A1 8/2005 Hunter ...................... 424/423
2005/0170448 A1 8/2005 Burson ....................... 435/14
2005/0171567 A1 8/2005 DeHart ...................... 606/181
2005/0172021 A1 8/2005 Brown ...................... 709/224
2005/0172022 A1 8/2005 Brown ...................... 709/224
2005/0173245 A1 8/2005 Feldman ............... 204/403.01
2005/0173246 A1 8/2005 Hodges ................ 204/403.11
2005/0175509 A1 8/2005 Nakaminami ........... 422/82.03
2005/0176084 A1 8/2005 Burkoth ....................... 435/14
2005/0176133 A1 8/2005 Miyashita ............... 435/287.1
2005/0177071 A1 8/2005 Nakayama ................. 600/583
2005/0177201 A1 8/2005 Freeman ..................... 607/46
2005/0177398 A1 8/2005 Watanabe ...................... 705/3
2005/0178218 A1 8/2005 Montagu ................ 73/864.34
2005/0181010 A1 8/2005 Hunter ...................... 424/423
2005/0181497 A1 8/2005 Salto ...................... 435/287.1
2005/0182307 A1 8/2005 Currie ....................... 600/300
2005/0187439 A1 8/2005 Blank ........................ 600/310
2005/0187444 A1 8/2005 Hubner ...................... 600/322
2005/0192488 A1 9/2005 Bryenton ................... 600/301
2005/0196821 A1 9/2005 Monfre ....................... 435/14
2005/0197666 A1 9/2005 Raney ....................... 606/181
2005/0201897 A1 9/2005 Zimmer .................. 422/82.05

2005/0202567 A1 9/2005 Zanzucchi .................. 436/95
2005/0203358 A1 9/2005 Monfre ...................... 600/331
2005/0203364 A1 9/2005 Monfre ...................... 600/365
2005/0204939 A1 9/2005 Krejci ....................... 101/129
2005/0205422 A1 9/2005 Moser .................. 204/403.06
2005/0205816 A1 9/2005 Hayenga ................... 251/61.1
2005/0209515 A1 9/2005 Hockersmith .............. 600/316
2005/0209564 A1 9/2005 Bonner ...................... 604/173
2005/0209625 A1 9/2005 Chan ......................... 606/181
2005/0211571 A1 9/2005 Schulein ................. 205/777.5
2005/0211572 A1 9/2005 Buck ......................... 205/778
2005/0214881 A1 9/2005 Azarnia .................... 435/7.92
2005/0214892 A1 9/2005 Kovatchev .................. 435/25
2005/0215871 A1 9/2005 Feldman .................... 600/309
2005/0215872 A1 9/2005 Berner ...................... 600/347
2005/0215923 A1 9/2005 Wiegel ...................... 600/573
2005/0215925 A1 9/2005 Chan ......................... 600/583
2005/0216046 A1 9/2005 Yeoh ......................... 606/181
2005/0218024 A1 10/2005 Lang ......................... 206/438
2005/0221276 A1 10/2005 Rozakis ........................ 435/4
2005/0221470 A1 10/2005 Matsumoto ............. 435/287.1
2005/0222599 A1 10/2005 Czernecki .................. 606/182
2005/0227372 A1 10/2005 Khan ........................ 436/514
2005/0228242 A1 10/2005 Kawamura ................. 600/300
2005/0228883 A1 10/2005 Brown ...................... 709/224
2005/0230252 A1 10/2005 Tsai .......................... 204/450
2005/0230253 A1 10/2005 Marquant .................. 204/451
2005/0232813 A1 10/2005 Karmali ...................... 422/58
2005/0232815 A1 10/2005 Ruhl .......................... 422/66
2005/0234368 A1 10/2005 Wong ........................ 600/583
2005/0234486 A1 10/2005 Allen ........................ 606/181
2005/0234487 A1 10/2005 Shi ........................... 600/181
2005/0234488 A1 10/2005 Allen ........................ 606/181
2005/0234489 A1 10/2005 Allen ........................ 606/181
2005/0234490 A1 10/2005 Allen ........................ 606/181
2005/0234491 A1 10/2005 Allen ........................ 606/181
2005/0234492 A1 10/2005 Tsai .......................... 606/181
2005/0234494 A1 10/2005 Conway .................... 606/181
2005/0234495 A1 10/2005 Schraga ..................... 606/181
2005/0235060 A1 10/2005 Brown ...................... 709/224
2005/0239154 A1 10/2005 Feldman ..................... 435/14
2005/0239156 A1 10/2005 Drucker ...................... 435/14
2005/0239194 A1 10/2005 Takahashi ............... 435/287.2
2005/0240090 A1 10/2005 Ruchti ....................... 600/316
2005/0240119 A1 10/2005 Draudt ...................... 600/583
2005/0240207 A1 10/2005 Marshall .................... 606/181
2005/0240778 A1 10/2005 Saito ......................... 713/186
2005/0245798 A1 11/2005 Yamaguchi ................ 600/345
2005/0245843 A1 11/2005 Day .......................... 600/583
2005/0245844 A1 11/2005 Mace ........................ 600/583
2005/0245845 A1 11/2005 Roe .......................... 600/583
2005/0245846 A1 11/2005 Day .......................... 600/583
2005/0245954 A1 11/2005 Roe .......................... 606/181
2005/0245955 A1 11/2005 Schraga ..................... 606/181
2005/0256534 A1 11/2005 Alden ....................... 606/182
2005/0258035 A1 11/2005 Harding ................ 204/403.01
2005/0258036 A1 11/2005 Harding ................ 204/403.01
2005/0258050 A1 11/2005 Harding ..................... 205/775
2005/0265094 A1 12/2005 Harding ..................... 365/203
2005/0276133 A1 12/2005 Harding ..................... 365/203
2005/0278945 A1 12/2005 Feldman ...................... 29/830
2005/0279631 A1 12/2005 Celentano ............. 204/403.01
2005/0279647 A1 12/2005 Beaty ........................ 205/792
2005/0283094 A1 12/2005 Thym ........................ 600/583
2005/0284110 A1 12/2005 Lang .......................... 53/473
2005/0284757 A1 12/2005 Allen ........................ 204/400
2005/0287620 A1 12/2005 Heller ........................ 435/14
2005/0288637 A1 12/2005 Kuhr ......................... 604/204
2005/0288698 A1 12/2005 Matsumoto ................ 606/181
2005/0288699 A1 12/2005 Schraga ..................... 606/181
2006/0000549 A1 1/2006 Lang ......................... 156/320
2006/0003398 A1 1/2006 Heller ........................ 435/14
2006/0004270 A1 1/2006 Bedard ...................... 600/316
2006/0004271 A1 1/2006 Peyser ....................... 600/362
2006/0004272 A1 1/2006 Shah ......................... 600/365
2006/0006574 A1 1/2006 Lang ......................... 264/165
2006/0008389 A1 1/2006 Sacherer .................... 422/102
2006/0015129 A1 1/2006 Shahrokni .................. 606/181
2006/0016698 A1 1/2006 Lee ........................ 205/777.5
2006/0020228 A1 1/2006 Fowler ...................... 600/583
2006/0024774 A1 2/2006 Zocchi ....................... 435/14
2006/0025662 A1 2/2006 Buse ......................... 600/347
2006/0029979 A1 2/2006 Bai ........................... 435/7.1
2006/0029991 A1 2/2006 Hagino ....................... 435/14
2006/0030028 A1 2/2006 Nakaminami ............ 435/287.2
2006/0030788 A1 2/2006 Wong ........................ 600/583
2006/0034728 A1 2/2006 Kloepfer ................... 422/68.1
2006/0040333 A1 2/2006 Zocchi ....................... 435/14
2006/0047220 A1 3/2006 Sakata ....................... 600/583
2006/0047294 A1 3/2006 Mori ......................... 606/181
2006/0052723 A1 3/2006 Roe .......................... 600/583
2006/0052724 A1 3/2006 Roe .......................... 600/583
2006/0052809 A1 3/2006 Karbowniczek ........... 606/181
2006/0052810 A1 3/2006 Freeman .................... 606/181
2006/0058827 A1 3/2006 Sakata ....................... 606/181
2006/0058828 A1 3/2006 Shi ........................... 606/181
2006/0062852 A1 3/2006 Holmes ..................... 424/484
2006/0063988 A1 3/2006 Schurman .................. 600/316
2006/0064035 A1 3/2006 Wang ........................ 600/583
2006/0079739 A1 4/2006 Wang ........................ 600/300
2006/0079810 A1 4/2006 Patel ......................... 600/583
2006/0079811 A1 4/2006 Roe .......................... 600/583
2006/0079920 A1 4/2006 Schraga ..................... 606/181
2006/0081469 A1 4/2006 Lee ...................... 204/403.02
2006/0085020 A1 4/2006 Freeman .................... 606/181
2006/0085137 A1 4/2006 Bartkowiak ................. 702/19
2006/0086624 A1 4/2006 Tapsak ...................... 205/775
2006/0088945 A1 4/2006 Douglas ..................... 436/518
2006/0089566 A1 4/2006 DeHart ...................... 600/573
2006/0091006 A1 5/2006 Wang .................... 204/403.02
2006/0094944 A1 5/2006 Chuang ..................... 600/347
2006/0094947 A1 5/2006 Kovatchev ................. 600/365
2006/0094986 A1 5/2006 Neel .......................... 600/583
2006/0095061 A1 5/2006 Trautman .................. 606/185
2006/0096859 A1 5/2006 Lau ...................... 204/403.14
2006/0099107 A1 5/2006 Yamamoto ................... 422/57
2006/0099703 A1 5/2006 Choi ...................... 435/287.1
2006/0100542 A9 5/2006 Wong ........................ 600/583
2006/0100543 A1 5/2006 Raney ....................... 600/583
2006/0100654 A1 5/2006 Fukuda ...................... 606/181
2006/0100655 A1 5/2006 Leong ....................... 606/181
2006/0100656 A1 5/2006 Olsen ........................ 606/181
2006/0106373 A1 5/2006 Cahir ........................... 606/9
2006/0108236 A1 5/2006 Kasielke .................... 205/792
2006/0113187 A1 6/2006 Deng .................... 204/403.01
2006/0115857 A1 6/2006 Keen .......................... 435/7.1
2006/0116562 A1 6/2006 Acosta ...................... 600/316
2006/0116704 A1 6/2006 Ashby ....................... 606/167
2006/0116705 A1 6/2006 Schraga ..................... 606/181
2006/0119362 A1 6/2006 Kermani .................... 324/324
2006/0121547 A1 6/2006 McIntire ..................... 435/14
2006/0121625 A1 6/2006 Clemens .................... 436/514
2006/0121759 A1 6/2006 Kasai ........................ 439/188
2006/0122099 A1 6/2006 Aoki ............................ 514/3
2006/0122536 A1 6/2006 Haar ......................... 600/581
2006/0129065 A1 6/2006 Matsumoto ................ 600/583
2006/0129172 A1 6/2006 Crossman .................. 606/181
2006/0129173 A1 6/2006 Wilkinson .................. 606/181
2006/0134713 A1 6/2006 Rylatt ...................... 435/7.92
2006/0140457 A1 6/2006 Simshauser ................ 382/124
2006/0144704 A1 7/2006 Ghesquiere ............ 204/403.01
2006/0151323 A1 7/2006 Cho ..................... 204/403.04
2006/0155215 A1 7/2006 Cha .......................... 600/583
2006/0155316 A1 7/2006 Perez ........................ 606/181
2006/0155317 A1 7/2006 List ........................... 606/181
2006/0156796 A1 7/2006 Burke ...................... 73/61.44

| | | | | |
|---|---|---|---|---|
| 2006/0157362 | A1 | 7/2006 | Schraga | 206/363 |
| 2006/0161078 | A1 | 7/2006 | Schraga | 600/583 |
| 2006/0161194 | A1 | 7/2006 | Freeman | 606/185 |
| 2006/0166302 | A1 | 7/2006 | Clarke | 435/25 |
| 2006/0167382 | A1 | 7/2006 | Deshmukh | 600/583 |
| 2006/1051342 | | 7/2006 | Yaguchi | 206/306 |
| 2006/0169599 | A1 | 8/2006 | Feldman | 205/792 |
| 2006/0173254 | A1 | 8/2006 | Acosta | 600/316 |
| 2006/0173255 | A1 | 8/2006 | Acosta | 600/316 |
| 2006/0173379 | A1 | 8/2006 | Rasch-Menges | 600/583 |
| 2006/0173380 | A1 | 8/2006 | Hoenes | 600/583 |
| 2006/0173478 | A1 | 8/2006 | Schraga | 606/181 |
| 2006/0175216 | A1 | 8/2006 | Freeman | 206/363 |
| 2006/0178573 | A1 | 8/2006 | Kermani | 600/347 |
| 2006/0178599 | A1 | 8/2006 | Faupel | 600/578 |
| 2006/0178600 | A1 | 8/2006 | Kennedy | 600/584 |
| 2006/0178686 | A1 | 8/2006 | Schraga | 606/181 |
| 2006/0178687 | A1 | 8/2006 | Freeman | 606/181 |
| 2006/0178688 | A1 | 8/2006 | Freeman | 606/181 |
| 2006/0178689 | A1 | 8/2006 | Freeman | 606/181 |
| 2006/0178690 | A1 | 8/2006 | Freeman | 606/181 |
| 2006/0183871 | A1 | 8/2006 | Ward | 525/464 |
| 2006/0183983 | A1 | 8/2006 | Acosta | 600/316 |
| 2006/0184101 | A1 | 8/2006 | Srinivasan | 604/68 |
| 2006/0188395 | A1 | 8/2006 | Taniike | 422/57 |
| 2006/0189895 | A1 | 8/2006 | Neel | 600/584 |
| 2006/0191787 | A1 | 8/2006 | Wang | 204/400 |
| 2006/0195023 | A1 | 8/2006 | Acosta | 600/316 |
| 2006/0195047 | A1 | 8/2006 | Freeman | 600/583 |
| 2006/0195128 | A1 | 8/2006 | Alden | 606/181 |
| 2006/0195129 | A1 | 8/2006 | Freeman | 606/181 |
| 2006/0195130 | A1 | 8/2006 | Freeman | 606/181 |
| 2006/0195131 | A1 | 8/2006 | Freeman | 606/181 |
| 2006/0195132 | A1 | 8/2006 | Freeman | 606/181 |
| 2006/0195133 | A1 | 8/2006 | Freeman | 606/181 |
| 2006/0196031 | A1 | 9/2006 | Hoenes | 29/432 |
| 2006/0196795 | A1 | 9/2006 | Windus-Smith | 206/438 |
| 2006/0200044 | A1 | 9/2006 | Freeman | 600/583 |
| 2006/0200045 | A1 | 9/2006 | Roe | 600/583 |
| 2006/0200046 | A1 | 9/2006 | Windus-Smith | 600/583 |
| 2006/0200181 | A1 | 9/2006 | Fukuzawa | 606/181 |
| 2006/0200981 | A1 | 9/2006 | Bhullar | 29/847 |
| 2006/0200982 | A1 | 9/2006 | Bhullar | 29/847 |
| 2006/0204399 | A1 | 9/2006 | Freeman | 422/58 |
| 2006/0205029 | A1 | 9/2006 | Heller | 435/25 |
| 2006/0205060 | A1 | 9/2006 | Kim | 435/287.2 |
| 2006/0206135 | A1 | 9/2006 | Uehata | 606/181 |
| 2006/0211127 | A1 | 9/2006 | Iwaki | 436/169 |
| 2006/0211927 | A1 | 9/2006 | Acosta | 600/316 |
| 2006/0211931 | A1 | 9/2006 | Blank | 600/344 |
| 2006/0219551 | A1 | 10/2006 | Edelbrock | 204/403.14 |
| 2006/0222567 | A1 | 10/2006 | Kloepfer | 422/68.1 |
| 2006/0224171 | A1 | 10/2006 | Sakata | 606/181 |
| 2006/0224172 | A1 | 10/2006 | Levaughn | 606/181 |
| 2006/0229532 | A1 | 10/2006 | Wong | 600/583 |
| 2006/0229533 | A1 | 10/2006 | Hoenes | 600/584 |
| 2006/0229651 | A1 | 10/2006 | Marshall | 606/181 |
| 2006/0231396 | A1 | 10/2006 | Yamaoka | 204/403.14 |
| 2006/0231418 | A1 | 10/2006 | Harding | 205/775 |
| 2006/0231442 | A1 | 10/2006 | Windus-Smith | 206/438 |
| 2006/0234369 | A1 | 10/2006 | Sih | 435/287.1 |
| 2006/0235284 | A1 | 10/2006 | Lee | 600/345 |
| 2006/0235454 | A1 | 10/2006 | LeVaughn | 606/181 |
| 2006/0241517 | A1 | 10/2006 | Fowler | 600/583 |
| 2006/0241666 | A1 | 10/2006 | Briggs | 606/181 |
| 2006/0241667 | A1 | 10/2006 | Freeman | 606/181 |
| 2006/0241668 | A1 | 10/2006 | Schraga | 606/181 |
| 2006/0241669 | A1 | 10/2006 | Stout | 606/182 |
| 2006/0247554 | A1 | 11/2006 | Roe | 600/583 |
| 2006/0247555 | A1 | 11/2006 | Harttig | 600/584 |
| 2006/0247670 | A1 | 11/2006 | LeVaughn | 606/181 |
| 2006/0247671 | A1 | 11/2006 | Levaughn | 606/182 |
| 2006/0259057 | A1 | 11/2006 | Kim | 606/181 |
| 2006/0259058 | A1 | 11/2006 | Schiff | 606/181 |
| 2006/0259060 | A1 | 11/2006 | Whitson | 606/182 |
| 2006/0264718 | A1 | 11/2006 | Ruchti | 600/310 |
| 2006/0264996 | A1 | 11/2006 | Levaughn | 606/181 |
| 2006/0264997 | A1 | 11/2006 | Colonna | 606/181 |
| 2006/0271083 | A1 | 11/2006 | Boecker | 606/181 |
| 2006/0271084 | A1 | 11/2006 | Schraga | 606/182 |
| 2006/0276724 | A1 | 12/2006 | Freeman | 600/583 |
| 2006/0277048 | A1 | 12/2006 | Kintzig | 704/275 |
| 2006/0278545 | A1 | 12/2006 | Henning | 206/363 |
| 2006/0282109 | A1 | 12/2006 | Jansen | 606/181 |
| 2006/0286620 | A1 | 12/2006 | Werner | 435/14 |
| 2006/0287664 | A1 | 12/2006 | Grage | 606/181 |
| 2006/0293577 | A1 | 12/2006 | Morrison | 600/365 |
| 2007/0004989 | A1 | 1/2007 | Dhillon | 600/583 |
| 2007/0004990 | A1 | 1/2007 | Kistner | 600/583 |
| 2007/0007183 | A1 | 1/2007 | Schulat | 209/573 |
| 2007/0009381 | A1 | 1/2007 | Schulat | 422/58 |
| 2007/0010839 | A1 | 1/2007 | Galloway | 606/167 |
| 2007/0010841 | A1 | 1/2007 | Teo | 606/181 |
| 2007/0015978 | A1 | 1/2007 | Kanayama | 600/310 |
| 2007/0016079 | A1 | 1/2007 | Freeman | 600/476 |
| 2007/0016103 | A1 | 1/2007 | Calasso | 600/583 |
| 2007/0016104 | A1 | 1/2007 | Jansen | 600/583 |

FOREIGN PATENT DOCUMENTS

| | | |
|---|---|---|
| EP | 0320109 | 6/1989 |
| EP | 0170375 | 5/1990 |
| EP | 0136362 | 12/1990 |
| EP | 0453283 | 10/1991 |
| EP | 0263948 | 2/1992 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0560336 | 5/1998 |
| EP | 0878 708 | 11/1998 |
| EP | 0505475 | 3/1999 |
| EP | 0901018 | 3/1999 |
| EP | 0470649 | 6/1999 |
| EP | 0847447 | 11/1999 |
| EP | 0964059 | 12/1999 |
| EP | 0969097 | 1/2000 |
| EP | 1021950 | 7/2000 |
| EP | 0894869 | 2/2001 |
| EP | 1074832 | 2/2001 |
| EP | 1093854 | 4/2001 |
| EP | 1114995 | 7/2001 |
| EP | 0736607 | 8/2001 |
| EP | 0874984 | 11/2001 |
| EP | 0730037 | 12/2001 |
| EP | 0636879 | 1/2002 |
| EP | 01174083 | 1/2002 |
| EP | 0851224 | 3/2002 |
| EP | 0759553 | 5/2002 |
| EP | 0856586 | 5/2002 |
| EP | 0817809 | 7/2002 |
| EP | 0872728 | 7/2002 |

| | | |
|---|---|---|
| EP | 0795748 | 8/2002 |
| EP | 0685737 | 9/2002 |
| EP | 0958495 | 11/2002 |
| EP | 0937249 | 12/2002 |
| EP | 0880692 | 1/2004 |
| EP | 01374770 | 1/2004 |
| EP | 1246688 | 5/2004 |
| EP | 1502614 | 2/2005 |
| GB | 2168815 | 6/1986 |
| WO | WO 80/01389 | 7/1980 |
| WO | WO 85/04089 | 9/1985 |
| WO | WO 86/07632 | 12/1985 |
| WO | WO 91/09139 | 6/1991 |
| WO | WO 93/06979 | 4/1993 |
| WO | WO 93/25898 | 12/1993 |
| WO | WO 94/27140 | 11/1994 |
| WO | WO 94/29703 | 12/1994 |
| WO | WO 94/29704 | 12/1994 |
| WO | WO 94/29731 | 12/1994 |
| WO | WO 95/00662 | 1/1995 |
| WO | WO 95/10223 | 4/1995 |
| WO | WO 95/22597 | 8/1995 |
| WO | WO 96/30431 | 10/1996 |
| WO | WO 97/02359 | 1/1997 |
| WO | WO 97/02487 | 1/1997 |
| WO | WO 97/16679 | 5/1997 |
| WO | WO 97/18464 | 5/1997 |
| WO | WO 97/30344 | 8/1997 |
| WO | WO 97/42882 | 11/1997 |
| WO | WO 97/45720 | 12/1997 |
| WO | WO 98/03431 | 1/1998 |
| WO | WO 98/12539 | 3/1998 |
| WO | WO 98/19159 | 5/1998 |
| WO | WO 98/20332 | 5/1998 |
| WO | WO 98/20348 | 5/1998 |
| WO | WO 98/24366 | 6/1998 |
| WO | WO 98/35225 | 8/1998 |
| WO | WO 99/03584 | 1/1999 |
| WO | WO 99/05966 | 2/1999 |
| WO | WO 99/13100 | 3/1999 |
| WO | WO 99/17854 | 4/1999 |
| WO | WO 99/18532 | 4/1999 |
| WO | WO 99/19507 | 4/1999 |
| WO | WO 99/19717 | 4/1999 |
| WO | WO 99/27483 | 6/1999 |
| WO | WO 99/27852 | 6/1999 |
| WO | WO 99/62576 | 12/1999 |
| WO | WO 99/64580 | 12/1999 |
| WO | WO 00/06024 | 2/2000 |
| WO | WO 00/09184 | 2/2000 |
| WO | WO 00/11578 | 3/2000 |
| WO | WO 00/15103 | 3/2000 |
| WO | WO 00/17799 | 3/2000 |
| WO | WO 00/17800 | 3/2000 |
| WO | WO 00/18293 | 4/2000 |
| WO | WO 00/19346 | 4/2000 |
| WO | WO 00/30186 | 5/2000 |
| WO | WO 00/32097 | 6/2000 |
| WO | WO 00/32098 | 6/2000 |
| WO | WO 00/33236 | 6/2000 |
| WO | WO 00/39914 | 7/2000 |
| WO | WO 00/42422 | 7/2000 |
| WO | WO 00/44084 | 7/2000 |
| WO | WO 00/50771 | 8/2000 |
| WO | WO 00/60340 | 10/2000 |
| WO | WO 00/64022 | 10/2000 |
| WO | WO 00/67245 | 11/2000 |
| WO | WO 00/67268 | 11/2000 |
| WO | WO 00/72452 | 11/2000 |
| WO | WO 01/00090 | 1/2001 |
| WO | WO 01/75433 | 3/2001 |
| WO | WO 01/23885 | 4/2001 |
| WO | WO 01/25775 | 4/2001 |
| WO | WO 01/26813 | 4/2001 |
| WO | WO 01/33216 | 5/2001 |
| WO | WO 01/34029 | 5/2001 |
| WO | WO 01/36955 | 5/2001 |
| WO | WO 01/37174 | 5/2001 |
| WO | WO 01/40788 | 7/2001 |
| WO | WO 01/57510 | 8/2001 |
| WO | WO 01/64105 | 9/2001 |
| WO | WO 01/66010 | 9/2001 |
| WO | WO 01/69505 | 9/2001 |
| WO | WO 01/72225 | 10/2001 |
| WO | WO 01/73124 | 10/2001 |
| WO | WO 01/73395 | 10/2001 |
| WO | WO 01/89691 | 11/2001 |
| WO | WO 02/00101 | 1/2002 |
| WO | WO 02/02796 | 1/2002 |
| WO | WO 02/08750 | 1/2002 |
| WO | WO 02/08753 | 1/2002 |
| WO | WO 02/08950 | 1/2002 |
| WO | WO 02/18940 | 3/2002 |
| WO | WO 02/21317 | 3/2002 |
| WO | WO 02/25551 | 3/2002 |
| WO | WO 02/32559 | 4/2002 |
| WO | WO 02/41227 | 5/2002 |
| WO | WO 02/41779 | 5/2002 |
| WO | WO 02/44948 | 6/2002 |
| WO | WO 02/059734 | 8/2002 |
| WO | WO 02/069791 | 9/2002 |
| WO | WO 02/077638 | 10/2002 |
| WO | WO 02/100251 | 12/2002 |
| WO | WO 02/100252 | 12/2002 |
| WO | WO 02/100253 | 12/2002 |
| WO | WO 02/100254 | 12/2002 |
| WO | WO 02/100460 | 12/2002 |
| WO | WO 02/100461 | 12/2002 |
| WO | WO 02/101343 | 12/2002 |
| WO | WO 02/101359 | 12/2002 |
| WO | WO 03/023389 | 3/2003 |
| WO | WO 03/042691 | 5/2003 |
| WO | WO 03/000321 | 6/2003 |
| WO | WO 03/045557 | 6/2003 |
| WO | WO 03/046542 | 6/2003 |
| WO | WO 03/049609 | 6/2003 |
| WO | WO 03/050534 | 6/2003 |
| WO | WO 03/070099 | 8/2003 |
| WO | WO 03/071940 | 9/2003 |
| WO | WO 03/094752 | 11/2003 |
| WO | WO 03/101297 | 12/2003 |
| WO | WO 04/008130 | 1/2004 |
| WO | WO 2004/022133 | 3/2004 |
| WO | WO 04/026130 | 4/2004 |
| WO | WO 04/041082 | 5/2004 |
| WO | WO 2004/040285 A2 | 5/2004 |
| WO | WO 2004/040287 A1 | 5/2004 |
| WO | WO 2004/040948 | 5/2004 |
| WO | WO 04/054455 | 7/2004 |
| WO | WO 04/060174 | 7/2004 |
| WO | WO 04/060446 | 7/2004 |
| WO | WO 03/066128 | 8/2004 |
| WO | WO 04/091693 | 10/2004 |
| WO | WO 2004/098405 | 11/2004 |
| WO | WO 04/107964 | 12/2004 |
| WO | WO 04/107975 | 12/2004 |
| WO | WO 04/112602 | 12/2004 |
| WO | WO 2004/003147 | 12/2004 |
| WO | WO 2004/107964 | 12/2004 |
| WO | WO 05/001418 | 1/2005 |
| WO | WO 2005/001418 | 1/2005 |
| WO | WO 2005/006939 | 1/2005 |
| WO | WO 2005/011774 | 2/2005 |
| WO | WO 2005/016125 | 2/2005 |
| WO | WO 2005/018425 | 3/2005 |
| WO | WO 2005/018430 | 3/2005 |

| | | | |
|---|---|---|---|
| WO | WO 2005/018454 | | 3/2005 |
| WO | WO 2005/018709 | | 3/2005 |
| WO | WO 2005/018710 | | 3/2005 |
| WO | WO 2005/018711 | | 3/2005 |
| WO | WO 2005/022143 | | 3/2005 |
| WO | WO 2005/023088 | | 3/2005 |
| WO | WO 2005/033659 | | 4/2005 |
| WO | WO 2005/034720 | | 4/2005 |
| WO | WO 2005/034721 | | 4/2005 |
| WO | WO 2005/034741 | | 4/2005 |
| WO | WO 2005/034778 | | 4/2005 |
| WO | WO 2005/035017 | | 4/2005 |
| WO | WO 2005/035018 | | 4/2005 |
| WO | WO 2005/037095 | | 4/2005 |
| WO | WO 2005/046477 | | 5/2005 |
| WO | WO 2005/065399 | | 7/2005 |
| WO | WO 2005/065414 | | 7/2005 |
| WO | WO 2005/065415 | | 7/2005 |
| WO | WO 20065545 | A2 | 7/2005 |
| WO | WO 2005/072604 | | 8/2005 |
| WO | WO 2005/084557 | | 9/2005 |
| WO | WO 2005/116622 | | 12/2005 |
| WO | WO 2005/119234 | | 12/2005 |
| WO | WO 2005/121759 | | 12/2005 |
| WO | WO 2006/001973 | | 1/2006 |
| WO | WO 2006/011062 | | 2/2006 |
| WO | WO 2006/013045 | | 2/2006 |
| WO | WO 2006/027702 | A2 | 3/2006 |
| WO | WO 2006/032391 | | 3/2006 |
| WO | WO 2006/072004 | | 7/2006 |

* cited by examiner

THERMAL REGULATION OF FLUIDIC SAMPLES WITHIN A DIAGNOSTIC CARTRIDGE

FIELD OF THE INVENTION

The present invention is related to an apparatus and method for controlling temperature in a reaction vessel. More particularly, the invention relates to Point-of-Care ("POC") analytical devices with thermal regulation of reactance in a cartridge for body fluid diagnostics. The invention uses a localized heat source. The heat source may be a heat generator. such as resistive heaters (using directly or inductively aenerated current) or Peltier heaters. placed internal or external to the cartridge, or it may generate heat directly through absorption of electromagnetic radiation from, for example. light emitting diodes ("LEDs") or vertical cavity surface emitting lasers ("VCSELs").

BACKGROUND OF THE INVENTION

Conducting chemical reactions on the microscopic scale in a miniature analytical device, while being able to precisely vary reaction parameters such as concentration and temperature has been made possible by trends in microfluidics and combinatorial chemistry. Such control requires thermal regulation using a localized heat source on the miniature analytical device.

The term "miniature analytical device" refers to a device for conducting chemical and biological analytical tests ("assays") on a smaller scale as related to bench-top analytical equipment. Because such devices are small and light weight, they can be portable as well as modular with disposable and reusable portions. The portability of such devices makes it possible to carry out such reactions near the patient, at the point of care, rather than in the laboratory.

The term "localized heat source" refers to a source of heat which is proximate to the substance to be heated. Such a source can comprise multiple point sources of heat. One particular area in which being able to carry out chemical and biological reactions on a miniature device in the field has great importance is the area of medical diagnostics of bodily fluids such as blood.

Medical diagnostics of bodily fluids can involve several assays using a variety of assay elements. The term "reactant" refers to chemicals involved in a synthetic reaction, or assay elements such as body fluid samples (such as blood), washes, and reagent chemicals. Sensing methods for blood metabolites such as $pO_2$, $pCO_2$, $Na^+$, $Ca^{++}$, $K^+$, glucose or clinical parameters such as blood pH, hematocrit, and coagulation and hemoglobin factors include electrochemical, chemiluminescence, optical, electrical, mechanical and other methods.

The home-care or self-analysis by patients has been facilitated by miniature analytical devices that can analyze body fluids. Many POC tests are performed using capillary whole blood. Typically, a drop of blood for analysis is obtained by making a small incision in the fingertip or forearm, creating a small wound, which generates a small blood droplet on the surface of the skin. Moving tests closer to the patient's side by using miniature analytical devices, improves both the testing process and the clinical data information management, which in turn has a dramatic impact on both patient outcomes and costs to the health care system.

Some of the desired biochemical tests require a specified and stabilized temperature for accurate and reportable measurements. Prior solutions to the problem of controlled temperature included large instruments with substantial temperature-controlled zones that required significant electrical power to provide heating.

The term "heating" refers to adding heat to a substance to raise its temperature and removing heat from a substance to reduce its temperature. The term "thermal regulation" refers to modifying heating to increase, decrease, or maintain the temperature of a substance to a desired temperature.

Thermal regulation of reactants or assay elements can be achieved through bulk heating of the cartridge using heaters such as electrical resistance heaters, Peltier heating and cooling cells, air heaters, or infrared heaters. These bulk-heating systems are usually large, and have generous energy supplies. POC devices require smaller volumes than bench-top systems. POC device volumes range between $1\times10^{-1}$ and $1\times10^{3}$ microliters. More specifically, a POC diagnostic device can heat volumes of 1-5 micro liters of assay elements, such as a blood sample, and/or 100-500 micro liters of assay elements, such as reagents. Restricting the volume to be heated to the temperature-controlled zones reduces the amount of heat required and facilitates localized heating.

For a POC device to be truly portable, power management is a critical issue. One method of limiting power usage is to localize heating to only those zones where heating is necessary. Localized heating provides lower power consumption and more rapid attainment of a specified reaction temperature. Such a localized approach to heating has the added benefit of minimizing the cost of manufacturing the disposable cartridge for diagnostic analysis. The localized heating elements needed for the rapid transmission of heat and the regulation of temperature can be located on the POC device and the assay elements to be heated can be located on the disposable cartridge. Such efficiencies in power usage can save battery life.

There have been attempts at designing thermal regulation devices for miniaturized reaction chambers for synthetic and diagnostic applications such as PCR amplification, nucleic acid hybridization, chemical labeling, and nucleic acid fragmentation. These attempts have focused on bulk resistive heating. Bulk resistive heating requires direct contact between the POC device and the cartridge with the reactance. Bulk resistive heating is inefficient and slow compared to localized heating because it heats the surrounding environment as it heats the assay elements contained within the cartridge. Bulk resistive heating increases the time it takes to increase the temperature of the reactance because the cartridge must be heated to the desired temperature. Localized heating shortens the distance over which external heating occurs, bypasses the cartridge with radiation directed to the reactance, or heats from within the reactance.

It is accordingly a primary object of the invention to localize heating to specific temperature-controlled zones in a cartridge using electromagnetic radiation, internal heat, or external heat. The advantages are that such localized heating does not require direct contact with the entire cartridge. The localized energy provided by these heat sources can be easily and accurately manipulated so that the amount of energy directed towards portions of the cartridge can be finely tuned and controlled so that the desired temperature is rapidly achieved and maintained. Heating by localized energy mainly affects the reactance themselves, rather than the entire cartridge and/or the environment.

SUMMARY OF THE INVENTION

In accordance with the invention, a miniature analytical device with thermal regulation comprises a localized heat source to regulate the temperature in an array of temperature-controlled zones containing reactance such as assay elements for body fluid analysis. Thermal regulation through electromagnetic radiation can be achieved through the absorbance of irradiation by molecules of the reactance or assay elements, for example, the water molecules in the body fluid sample. Electromagnetic radiation can be emitted by LEDs, VCSELs, or microwave sources. Resistive, inductive and Peltier heaters positioned within or adjoining the reactance can generate internal heat. External heat can be generated by resistive heaters in contact with the cartridge which in turn heat the reactance.

The electromagnetic radiation in the form of an infrared illumination emitter can be configured as an array of infrared light sources, such as infrared lamps, infrared lasers, infrared laser diodes, LEDs or VCSELs positioned such that they correspond to the array of temperature-controlled zones. These infrared light sources can generate infrared light at different wavelengths ranging between 0.775 and 7000 micrometers. A power supply can be coupled to the infrared light sources to provide a sufficient drive current to regulate the temperature-controlled zones and to modulate using a controller so that the miniature analytical device can rapidly increase and maintain the temperature of the reactance in the temperature-controlled zones.

A method for heating includes heating an array of temperature-controlled zones, measuring the temperature, modulating the localized heat source, and regulating the temperature. In another embodiment, the method can include a step of modifying at least one absorptive property of the reactance, including color, refractive index, or transmission path (by using shutters or an LED window).

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE EMBODIMENTS

Reference will now be made in detail to the present embodiments of the invention. Thermal regulation of the reactance can be accomplished through the use of electromagnetic radiation from an emitter. The term “emitter” refers to a non-contact electromagnetic radiation source including microwave, infrared, or ultra-violet light which manipulates intensity, direction, phase, color, and other properties of the light. In one embodiment, this electromagnetic radiation energy can be derived from an infrared light source, which emits light in the wavelengths known to heat water, which are typically in the wavelength range from about 0.775 to 7000 micrometers (775 to $7\times10^6$ nanometers). For example, the infrared activity absorption bands of sea water are 1.6, 2.1, 3.0, 4.7 and 6.9 micrometers with an absolute maximum for the absorption coefficient for water at around 3 micrometers.

The infrared wavelengths are directed to the temperature-controlled zones containing the reactance, and because the portion of the cartridge around the temperature-controlled zones can be made of a clear or translucent material, the infrared waves can act directly upon the reactance to increase or maintain the temperature in the temperature-controlled zone. The term “temperature-controlled zone” refers to the area of space in which the assay elements or reactance are contained for thermal regulation such that an increase in the temperature of such zone corresponds to an increase in the temperature of the assay elements or reactance. Although infrared heating of the assay elements can be the result of the cartridge itself absorbing the irradiation of the infrared light, infrared heating of the reactance is primarily caused by the direct action of the infrared wavelengths on the reactance themselves.

The portion of the cartridge containing the temperature-controlled zones can be made of a material that allows the penetration of infrared light wavelengths, such as quartz glass, glass, silicon, transparent plastics, and the like. In one embodiment, a lightweight inexpensive material that allows infrared light to pass through with little interference is desired for the disposable diagnostic cartridge.

Alternatively, the infrared energy can be focused on the temperature-controlled zones by means of infrared transmissible lenses so that the sample is homogeneously irradiated. This technique avoids “hotspots” that could otherwise result in the creation of undesirable temperature differences and/or gradients, or the partial boiling of the assay elements. The homogeneous treatment of the temperature-controlled zones with infrared energy therefore contributes to a sharper and more uniform temperature profile for thermal regulation of the assay elements. Moreover, rapid increase in temperature can be facilitated if the miniature analytical device has a flat temperature-controlled zone exposing a majority of the assay element to the infrared light so that there exists a high ratio of surface area in contact with infrared light to volume of temperature controlled zone.

Infrared heating can be effected in either one step, or numerous steps, depending on the desired application. For example, a particular methodology may require that the reactance be heated to a first temperature, maintained at that temperature for a given dwell time, then heated to a higher temperature, and so on. As many heating steps as necessary can be included. The method can include measuring the temperature, measuring the concentration, modulating the localized heat source, and regulating the temperature. Alternatively, the method can include steps for modifying the optical absorptive properties of the reactance, including modifying their color. Alternatively, the method can include varying the wavelength of light whether within the infrared spectrum or in the microwave or ultraviolet spectrum.

Similarly, each reactant can require a specified thermal regulation depending on the particular assay. The electromagnetic radiation emitter can be configured into an array of point sources of electromagnetic radiation. The miniature analytical device and the array of point sources of electromagnetic radiation allows many assays to be run simultaneously on one cartridge using a variety of reactants. In one embodiment, a variety of assays can be run using prepackaged assay elements, such as reagents, and one recently obtained assay element, such as blood.

In one embodiment, an infrared emitter can be a single source with lenses and reflectors directing the light to the temperature-controlled zones. Alternatively, an array of infrared light emitters can be positioned so as to correspond to an array of temperature-controlled zones containing reactants to directly provide localized heating for each temperature-controlled zone with a corresponding infrared light source. The infrared light source may be any means known in the art for generating the desired range of wavelengths in the infrared spectrum. Typically, the heating means will be an infrared source, such as an infrared lamp, an infrared diode laser, an infrared laser, an LED or a VCSEL. In one embodiment, LEDs or VCSELs can be used for their easy arrangement in arrays and low power consumption. The term “array” refers to any configuration on the miniature analytical device corresponding to the configuration of temperature-controlled zones on the cartridge to conduct thermal regulation for all synthetic and/or diagnostic reactions carried out on the cartridge. The infrared light source can be supplied drive current by a power supply and modulated by a controller such that the current from the power supply achieves the desired thermal regulation in the temperature-controlled zones.

VCSELs can be formed by using for example a GaInAs, GaAlInP, Fabry-Perot, or ZnSe material system to generate infrared light at wavelengths of, for example, 980 nanometers and a beam diameter of 8-10 micrometers. The VCSELs are constructed on chips with. for example. grown diamond, AIN or plain copper substrates to control the incidental heat flux created on the miniature analytical device by generating the infrared light. VCSELs have 15-50% conversion efficiency between the power it takes to run the VCSEL to the infrared power generated. Moreover, VCSELs allow for measurement of the concentration of compounds by optical tests known in the art. The cartridge can be configured such that a transparent material bounds both sides of the temperature-controlled zone. On one side, the VCSEL emits infrared light to thermally regulate the reactants or assay elements. On the other side, the infrared light transmitted through the reactants or assay elements can be measured to determine the concentration of a material within the reactants. The term “material” refers to the product-of-interest of the reaction whose concentration is to be measured or the analyte within the assay elements of which the assay is testing concentration.

In one embodiment, concentration of a material in the reactants can be measured by measuring the electromagnetic absorption of the reactants as is well known in the art of spectrophotometry. In another embodiment, the temperature of the reactants can be measured by measuring the electromagnetic emission of the reactants as is well know in the art of spectrophotometry.

In bench-top thermal regulation, assay elements such as blood have been heated to either 25° C. or 37° C. using infrared light energy. An added benefit of using optical energy such as infrared light consists of using optical means for measuring the temperature. Such means are well known in the art, and retain the benefit of non-contact between the miniature analytical device and the disposable cartridge. In one embodiment, the miniature analytical device can be configured with an array of temperature monitors to correspond to the temperature-controlled zones. The term “temperature monitor” refers to a device for measuring the temperature of the reactants or assay elements in the temperature-controlled zone, or measuring the temperature of the portion of the cartridge surrounding the temperature-controlled zone or the environment. A feedback loop, comprising providing the measured temperature to the controller, modulates the power supply to drive the infrared light sources so that the desired temperature is achieved with a smooth control curve and/or is maintained at the desired temperature.

In one embodiment, the localized heat source comprises intemal heat that can be generated by resistive, inductive and Peltier heaters positioned within or adjoining the reactants. In one embodiment, these heaters can be arranged in an array to correspond to the array of temperature-controlled zones. Resistive heaters use the effect of heating electrically resistive elements, by passing current through the elements. Inductive heaters use the effect of heating electrically conductive materials, such as metals, by inducing high frequency currents within the material. Peltier heaters use Peltier effect to generate heat by passing electric current through a bimetallic junction. In one embodiment, an array of electrical leads can be positioned to correspond to the array of heaters, such that the array of electrical leads on the miniature analytical device correspond to the heaters on the cartridge. In one embodiment, the heaters can comprise discrete elements such as microbeads or filings, or continuous elements such as meshes, pads, or nets. These elements can be manufactured into the cartridge during the fabrication process to best position the elements in the vicinity of the temperature-controlled zones.

In bench-top thermal regulation, assay elements such as blood have been heated to either 25° C. or 37° C. using infrared light energy. An added benefit of using optical energy such as infrared light consists of using optical means for measuring the temperature. Such means are well known in the art, and retain the benefit of non-contact between the miniature analytical device and the disposable cartridge. In one embodiment, the miniature analytical device can be configured with an array of temperature monitors to correspond to the temperature-controlled zones. The term “temperature monitor” refers to a device for measuring the temperature of the reactants or assay elements in the temperature-controlled zone, or measuring the temperature of the portion of the cartridge surrounding the temperature-controlled zone or the environment. A feedback loop, comprising providing the measured temperature to the controller, modulates the power supply to drive the infrared light sources so that the desired temperature is achieved with a smooth control curve and/or is maintained at the desired temperature.

In one embodiment, the localized heat source comprises intemal heat that can be generated by resistive, inductive and Peltier heaters positioned within or adjoining the reactants. In one embodiment, these heaters can be arranged in an array to correspond to the array of temperature-controlled zones. Resistive heaters use the effect of heating electrically resistive elements, by passing current through the elements. Inductive heaters use the effect of heating electrically conductive materials, such as metals, by inducing high frequency currents within the material. Peltier heaters use Peltier effect to generate heat by passing electric current through a bimetallic junction. In one embodiment, an array of electrical leads can be positioned to correspond to the array of heaters, such that the array of electrical leads on the miniature analytical device correspond to the heaters on the cartridge. In one embodiment, the heaters can comprise discrete elements such as microbeads or filings, or continuous elements such as meshes, pads, or nets. These elements can be manufactured into the cartridge during the fabrication process to best position the elements in the vicinity of the temperature-controlled zones.

In bench-top thermal regulation, assay elements such as blood have been heated to either 25° C. or 37° C. using infrared light energy. An added benefit of using optical energy such as infrared light consists of using optical means for measuring the temperature. Such means are well known in the art, and retain the benefit of non-contact between the miniature analytical device and the disposable cartridge. In one embodiment, the miniature analytical device can be configured with an array of temperature monitors to correspond to the temperature-controlled zones. The term "temperature monitor" refers to a device for measuring the temperature of the reactants or assay elements in the temperature-controlled zone, or measuring the temperature of the portion of the cartridge surrounding the temperature-controlled zone or the environment. A feedback loop, comprising providing the measured temperature to the controller, modulates the power supply to drive the infrared light sources so that the desired temperature is achieved with a smooth control curve and/or is maintained at the desired temperature.

In one embodiment, the localized heat source comprises intemal heat that can be generated by resistive, inductive and Peltier heaters positioned within or adjoining the reactants. In one embodiment, these heaters can be arranged in an array to correspond to the array of temperature-controlled zones. Resistive heaters use the effect of heating electrically resistive elements, by passing current through the elements. Inductive heaters use the effect of heating electrically conductive materials, such as metals, by inducing high frequency currents within the material. Peltier heaters use Peltier effect to generate heat by passing electric current through a bimetallic junction. In one embodiment, an array of electrical leads can be positioned to correspond to the array of heaters, such that the array of electrical leads on the miniature analytical device correspond to the heaters on the cartridge. In one embodiment, the heaters can comprise discrete elements such as microbeads or filings, or continuous elements such as meshes, pads, or nets. These elements can be manufactured into the cartridge during the fabrication process to best position the elements in the vicinity of the temperature-controlled zones.

In another embodiment, external heat can be generated by resistive heaters in contact with the cartridge, which in turn heats the reactants. These heaters can be arranged in a sandwich structure surrounding the broad, flat surfaces of the cartridge comprising a temperature-controlled zone such that the heaters are in close proximity or in contact with the cartridge at the temperature-controlled zones. Such placement minimizes the thermal path length and resistance through which heat travels. The heaters can be arranged in an array to correspond with the array of temperature-controlled zones.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A point of care miniature analytical device with thermal regulation comprising:

a cartridge comprising one or more portions constructed of a material, wherein the one or more portions define an array of temperature-controlled zones including reactants, wherein each said temperature-controlled zones is constrained by cartridge portions that surround an area of space in which a reactant is contained and confine the reactant from flowing into other of said temperature-controlled zones, and wherein the cartridge portions include clear or translucent portions that allow direct irradiation of reactant molecules to facilitate thermal regulation of the reactants and to transmit light through the reactants;

an array of infrared radiation emitting heat sources, wherein the array of heat sources is positioned to correspond to the array of temperature-controlled zones so that each heat source is arranged to provide temperature regulation to a corresponding temperature-controlled zone, and wherein one or more of the heat sources emit localized radiation to provide heating in the corresponding temperature-controlled zone;

an optical temperature monitor, not in contact with the cartridge and disposed adjacent to a portion of the cartridge surrounding the temperature controlled zones, that monitors reactant temperature by measuring electromagnetic radiation;

a controller comprising a modulator;

a power supply configured to supply drive current to the array of heat sources and coupled to the controller to provide that current from the power supply achieves the desired thermal regulation in the temperature-controlled zones;

a feedback loop configured to provide measured temperatures to the controller, and to modulate the power supply to drive the infrared light heat sources to achieve a desired temperature with a smooth control curve at the desired temperature, and an instrument for measurement of electromagnetic emission obtained from irradiation of the reactants with the infrared radiation emitting heat sources, wherein the transmission of infrared radiation through the reactants allows a determination of a concentration of a material within the reactants.

2. A point of care miniature analytical device with thermal regulation according to claim 1, wherein: the array of infrared radiation emitting heat sources comprise vertical cavity surface emitting laser light sources.

3. A point of care miniature analytical device with thermal regulation according to claim 1, wherein: the array of infrared radiation emitting heat sources comprise at least one light source chosen from a vertical cavity surface emitting laser light source, a light emitting diode, an infrared lamp, an infrared laser, and infrared diode laser.

4. A point of care miniature analytical device with thermal regulation according to claim 3, wherein:

at least one of the infrared radiation emitting heat sources in the array of heat sources generates infrared light of a different wavelength from the remainder of the infrared radiation emitting heat sources.

5. A point of care miniature analytical device with thermal regulation according to claim 3, wherein:

the at least one light source generates infrared light with a wavelength of at least 0.775 micrometers.

6. A point of care miniature analytical device with thermal regulation according to claim 3, wherein:

the at least one light source generates infrared light with a wavelength of at most 7000 micrometers.

7. A point of care miniature analytical device with thermal regulation according to claim 1, wherein:

the controller modulates the power supply based on a temperature measured from the zones.

8. A point of care miniature analytical device with thermal regulation according to claim 1, further comprising:

an array of temperature monitors, wherein the array of temperature monitors is positioned to correspond to the array of temperature-controlled zones.

9. A point of care miniature analytical device with thermal regulation according to claim 1, wherein:

the reactants comprise assay elements for body fluid analysis.

10. A point of care miniature analytical device with thermal regulation according to claim 1, wherein:

the array of heat sources provides a reactant temperature that is one or both of achieved with a smooth control curve or maintained at a desired temperature.

* * * * *